(12) United States Patent
Noelle

(10) Patent No.: US 8,415,154 B2
(45) Date of Patent: Apr. 9, 2013

(54) COMPOSITIONS AND METHODS FOR PRODUCING ADAPTIVE REGULATORY T CELLS

(75) Inventor: Randolph J. Noelle, Plainfield, NH (US)

(73) Assignee: Trustees of Dartmouth College, Hanover, NH (US)

(*) Notice: Subject to any disclaimer, the term of this patent is extended or adjusted under 35 U.S.C. 154(b) by 0 days.

(21) Appl. No.: 12/601,682

(22) PCT Filed: May 29, 2008

(86) PCT No.: PCT/US2008/065064
§ 371 (c)(1),
(2), (4) Date: Jan. 7, 2010

(87) PCT Pub. No.: WO2008/150853
PCT Pub. Date: Dec. 11, 2008

(65) Prior Publication Data
US 2010/0183575 A1    Jul. 22, 2010

Related U.S. Application Data

(60) Provisional application No. 60/940,533, filed on May 29, 2007.

(51) Int. Cl.
*C12N 5/00* (2006.01)
(52) U.S. Cl. ........ 435/377; 435/375; 435/325; 424/93.7
(58) Field of Classification Search .................. None
See application file for complete search history.

(56) References Cited

U.S. PATENT DOCUMENTS

| 2006/0233751 A1 | 10/2006 | Bluestone et al. | 424/85.2 |
| 2006/0263340 A1 | 11/2006 | Andrian et al. | 424/93.7 |

OTHER PUBLICATIONS

Benson M et al. 2007. All-trans retinoic acid mediates enhanced T reg cell growth, differentiation, and gut homing in the face of high levels of co-stimulation. J Exp Med 204: 1765-1774.*
Pino-Lagos K et al. Retinoic acid in the immune system. Annals of NY Acad Sci 1143: 170-187.*
Wherrett DK et al. 2011. Prevention of type 1 diabetes. Pediatr Clin N Am 58: 1257-1270. Abstract only.*
Annacker et al. "Essential Role for CD103 in the T Cell-Mediated Regulation of Experimental Colitis" The Journal of Experimental Medicine 2005 vol. 202(8): 1051-1061.
Berlin et al. "α4β7 Integrin Mediates Lymphocyte Binding to the Mucosal Vascular Addressin MAdCAM-1" Cell 1993 vol. 74(1): 185-195.
Bluestone, J.A. and Abbas, A.K. "Natural Versus Adaptive Regulatory T Cells" Nature Reviews Immunology 2003 vol. 3(3): 253-257.
Brode et al. "Cyclophosphamide-Induced Type-1 Diabetes in the NOD Mouse is Associated with a Reduction of CD4$^+$CD25$^+$Foxp3$^+$ Regulatory T Cells" The Journal of Immunology 2006 vol. 177: 6603-6612.
Chen et al. "Conversion of Peripheral CD4$^+$CD25$^-$ Naive T Cells to CD4$^+$CD25$^+$ Regulatory T Cells by TGF-β Induction of Transcription Factor Foxp3" The Journal of Experimental Medicine 2003 vol. 198(12): 1875-1886.
Clark, R. and Kupper, T. "Old Meets New: The Interaction Between Innate and Adaptive Immunity" J Invest Dermatol 2005 vol. 125: 629-637.
Cobbold et al. "Induction of foxP3$^+$ Regulatory T Cells in the Periphery of T Cell Receptor Transgenic Mice Tolerized to Transplants" The Journal of Immunology 2004 vol. 172(10): 6003-6010.
Fantini et al. "Cutting Edge: TGF-β Induces a Regulatory Phenotype in CD4$^+$CD25$^-$ T Cells through Foxp3 Induction and Down-Regulation of Smad7" The Journal of Immunology 2004 vol. 172(9): 5149-5153.
Fantini et al. "Transforming Growth Factor β Induced FoxP3$^+$ Regulatory T Cells Suppress Th1 Mediated Experimental Colitis" Gut 2006 vol. 55: 671-680.
Iwata et al. "Retinoic Acid Imprints Gut-Homing Specificity on T Cells" Immunity 2004 vol. 21: 527-538.
Izcue et al. "Regulatory T Cells Suppress Systemic and Mucosal Immune Activation to Control Intestinal Inflammation" Immunological Reviews 2006 vol. 212: 256-271.
Johansson-Lindbom et al. "Functional Specialization of Gut CD103$^+$ Dendritic Cells in the Regulation of Tissue-Selective T Cell Homing" The Journal of Experimental Medicine 2005 vol. 202(8): 1063-1073.
Karim et al. "Alloantigen-Induced CD25$^+$CD4$^+$ Regulatory T Cells Can Develop In Vivo from CD25$^-$CD4$^+$ Precursors in a Thymus-Independent Process" The Journal of Immunology 2004 vol. 172(2): 923-928.
Mora, J.R. and von Andrian, U.H. "T-Cell Homing Specificity and Plasticity: New Concepts and Future Challenges" Trends in Immunology 2006 vol. 27(5): 235-243.
Ochando et al. "Alloantigen-Presenting Plasmacytoid Dendritic Cells Mediate Tolerance to Vascularized Grafts" Nature Immunology 2006 vol. 7(6):652-662.
Park et al. "Acquisition of Anergic and Suppressive Activities in Transforming Growth Factor-β-Costimulated CD4$^+$CD25$^-$ T Cells" International Immunology 2004 vol. 16(8): 1203-1213.
Siewart et al. "Induction of Organ-Selective CD4$^+$ Regulatory T Cell Homing" European Journal of Immunology 2007 vol. 37(4): 978-989.
Wagner et al. "Critical Role for β7 Integrins in Formation of the Gut-Associated Lymphoid Tissue" Nature 1996 vol. 385: 366-370.
Zabel et al. "Human G Protein-Coupled Receptor GPR-9-6/CC Chemokine Receptor 9 Is Selectively Expressed on Intestinal Homing T Lymphocytes, Mucosal Lymphocytes, and Thymocytes and Is Required for Thymus-Expressed Chemokine-Mediated Chemotaxis" The Journal of Experimental Medicine 1999 vol. 190(9):1241-1255.
Zheng et al. "Natural and Induced CD4$^+$CD25$^+$ Cells Educate CD4$^+$CD25$^-$ Cells to Develop Suppressive Activity: The Role of Il-2, TGF-β, and IL-10" The Journal of Immunology 2004 vol. 172(9): 5213-5221.

* cited by examiner

*Primary Examiner* — Lora E Barnhart Driscoll
(74) *Attorney, Agent, or Firm* — Licata & Tyrrell P.C.

(57) ABSTRACT

The present invention relates to a method for producing adaptive regulatory T cells from effector T cells by contacting the effector T cells with retinoic acid. Adaptive regulatory T cells produced by this method are Foxp3+, home to the gut, and are refractory to reversion in vivo. As such, such cells find application in the treatment of autoimmune disease and facilitating transplantation tolerance.

2 Claims, 6 Drawing Sheets

COMPOSITIONS AND METHODS FOR PRODUCING ADAPTIVE REGULATORY T CELLS

INTRODUCTION

This application claims benefit of priority to U.S. Provisional Patent Application Ser. No. 60/940,533, filed May 29, 2007, the content of which is incorporated herein by reference in its entirety.

This invention was made in the course of research sponsored by the National Institutes of Health (NIH grant No. AI-48667). The U.S. government may have certain rights in this invention.

BACKGROUND OF THE INVENTION

T regulatory cells, also referred to as $T^{reg}$, function to temper the massive pro-inflammatory stimulus formed by commensal bacteria and dietary antigens within the gut. Evidence of their functional importance at suppressing gut inflammation is observed by the fact that their absence permits the onset of gut autoimmunity (Izcue, et al. (2006) *Immunol. Rev.* 212:256-271). The manipulation of $T^{reg}$ within the gut, therefore, provides an attractive avenue of therapeutic intervention in enforcing gut tolerance during times when the balance is shifted toward autoimmunity.

The ability of activated T cells to exit the blood and enter different tissues of the body is 'imprinted' upon them within the secondary lymphoid organs (SLOs) by dendritic cells (Mora, et al. (2003) *Nature* 424:88-93; Mora, et al. (2005) *J. Exp. Med.* 201:303-316). T cells homing to the small intestine lamina propria express the integrin $\alpha 4\beta 7$, which binds mucosal addressin cell adhesion molecule-1 (MAdCAM-1), and the chemokine receptor CCR9, whose ligand is secreted within the lamina propria (Berlin, et al. (1993) *Cell* 74:185-195; Wagner, et al. (1996) *Nature* 382:366-370; Zabel, et al. (1999) *J. Exp. Med.* 190:1241-1256; Mora & von Andrian (2006) *Trends Immunol.* 27:235-243). A population of dendritic cells (DCs) expressing the integrin $CD103^+$ which reside primarily within the lamina propria, peyer's patches and mesenteric lymph nodes are responsible for imprinting a gut-homing capacity on T cells by an all-trans retinoic acid-dependent mechanism (Izcue, et al. (2006) supra; Annacker, et al. (2005) *J. Exp. Med.* 202:1051-1061; Johansson-Lindbom, et al. (2005) *J. Exp. Med.* 202:1063-1073; Iwata, et al. (2004) *Immunity* 21:527-538). As such, the activation of CD4+ T cells in the presence of all-trans-retinoic acid (RA) induces robust expression of the gut-homing markers $\alpha 4\beta 7$ and CCR9 and a gut-homing capacity in vitro (Iwata, et al. (2004) supra). IL-10 and TGF$\beta$ have also been shown to polarize CD4 T cells into $T^{reg}$ cells (Clark & Kupper (2005) *J. Invest. Dermatol.* 125:629-637).

It has been shown that CD4+FoxP3-naïve T cells can be converted into CD4+FoxP3+ $T^{reg}$ (hereafter referred to as adaptive $T^{reg}$) exhibiting the same suppressive and phenotypic characteristics as thymically-derived, natural $T^{reg}$ both in vivo and in vitro (Cobbold, et al. (2004) *J. Immunol.* 172:6003-6010; Chen, et al. (2003) *J. Exp. Med.* 198:1875-1886; Park, et al. (2004) *Int. Immunol.* 16:1203-1213; Fantini, et al. (2006) *Gut* 55:671-680; Ochando, et al. (2006) *Nat. Immunol.* 7:652-662). This conversion is dependent upon TGFbeta1 and requires high doses of IL-2 (Chan, et al. (2003) supra; Zheng, et al. (2004) *J. Immunol.* 172:5213-5221; Fantini, et al. (2004) *J. Immunol.* 172:5149-5153). Further, dendritic cells from mesenteric and peripheral lymph nodes (LN), or retinoic acid and IL-12 have been shown to function as polarizing compounds to induce mucosa- and skin-seeking $T^{reg}$, respectively (Siewert, et al. (2007) *Eur. J. Immunol.* 37(4): 978-89). Moreover, the use of adaptive $T^{reg}$ as a means of inducing tolerance has been demonstrated in numerous settings including inflammatory bowel disease and transplantation models (Cobbold, et al. (2004) supra; Fantini, et al. (2006) supra; Ochando, et al. (2006) supra; Karim, et al. (2004) *J. Immunol.* 172:923-928).

Improving the potency of the adaptive reg $T^{reg}$ treatments is of great clinical interest, and harnessing imprinting mechanisms in order to target adaptive $T^{reg}$ to a specific organ in need of immunosuppression is one means to this end.

SUMMARY OF THE INVENTION

The present invention relates to an isolated population of retinoic acid-induced adaptive regulatory T cells characterized as CD4+, Foxp3+, $\alpha 4\beta 7+$, CCR9+, and CD103+ cells which are refractory to reversion in vivo. The present invention also provides a method for producing such cells by contacting an isolated effector T cell population with a retinoic acid thereby producing a population of retinoic acid-induced adaptive regulatory T cells. In one embodiment, the method further includes contacting the effector T cell with a regulatory T cell differentiation composition containing a costimulatory agent, or a second regulatory T cell stimulatory agent, or combination thereof. In another embodiment, the method further includes contacting the effector T cell with an autoantigen-specific regulatory T cell stimulatory composition.

The present invention also relates to methods for preventing or treating an autoimmune response na facilitating transplant tolerance by comprising administering to a subject in need of treatment an effective amount of the isolated population of retinoic acid-induced adaptive regulatory T cells of the invention.

BRIEF DESCRIPTION OF THE DRAWINGS

FIG. 4 shows that retinoic acid allows adaptive $T^{reg}$ generation in the presence of co-stimulation.

FIG. 7 shows how short and long-term Vitamin A(VitA)-deficiency impacts peripheral tolerance in graft survival.

DETAILED DESCRIPTION OF THE INVENTION

Figure 1:
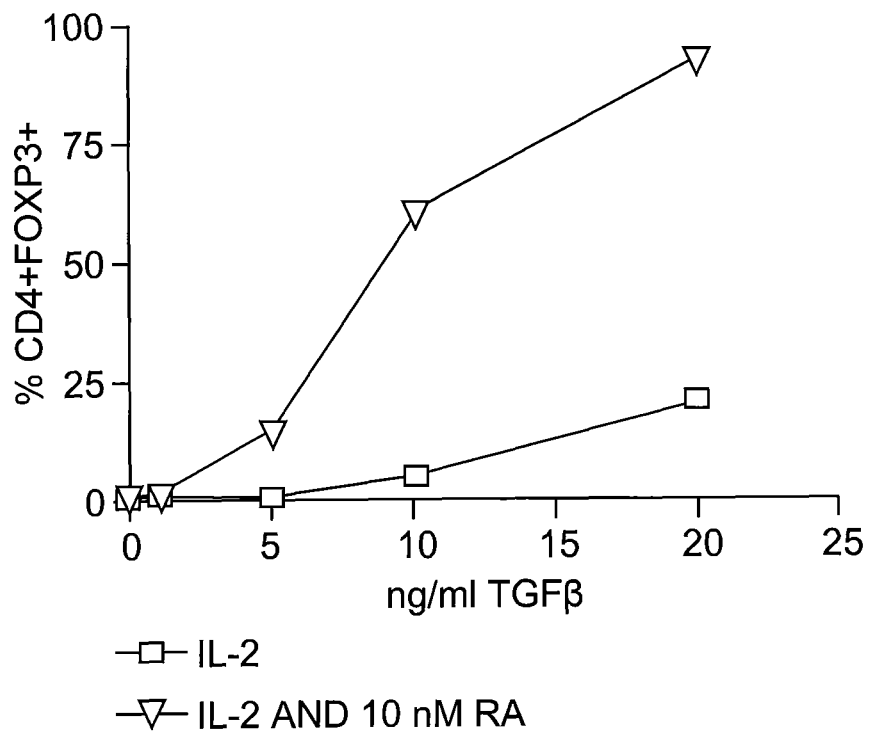
FIG. 1 shows Foxp3/GFP expression by CD4+ cells as a function of titrating concentrations of TGF$\beta$1+/− retinoic acid. IL-2 concentrations were kept constant, +/− retinoic acid, with TGF$\beta$1 (20, 10, 5, 1 and 0 ng/ml) titrated with percent Foxp3/GFP expressing cells plotted against TGF$\beta$1 concentration.

It has now been shown that retinoic acid can be used to generate a unique population of adaptive regulatory T (aT$^{reg}$) cells. Advantageously, the instant method employs a readily available starting material, i.e., effector T cells, for production of a homogeneous population of cells with regulatory capacity in vivo. Under conditions that favor the differentiation of aT$^{reg}$ (TGFβ1 and IL-2) in vitro, the inclusion of retinoic acid unexpectedly induces nearly 100% of CD4+ T cells to express Foxp3; greatly increases the proliferation of these cells; results in a net increase in Foxp3+ T cells; imprints their homing to the gut; allows Foxp3 induction in the presence of high levels of co-stimulation by uncoupling co-stimulation from inhibiting of Foxp3 induction; and induces T$^{reg}$ that are more refractory to reversion in vivo. The recognition that retinoic acid induces gut imprinting together with the finding that retinoic acid enhances conversion, differentiation and expansion of aT$^{reg}$, indicates that retinoic acid production in vivo may drive both the imprinting and aT$^{reg}$ development in the face of overt inflammation. Furthermore, the regional production of retinoic acid in tolerant sites likely plays an extremely important role in the development of "acquired immune privilege" (Cobbold, et al (2006) Immunol. Rev. 213:239-55; Waldmann (2006) Nature 442:987-8; Waldmann, et al. (2006) Immunol. Rev. 212:301-13), a term used to describe sites of anatomic tolerance. Additional data show that retinoic acid deprivation ablates graft survival in an allograft tolerance model, where graft survival is dependent on the differentiation and infiltration of aT$^{reg}$ into the graft. Together these in vitro and in vivo data show that retinoic acid is critical for the development of peripheral tolerance and establishes the therapeutic intervention in T$^{reg}$-dependent peripheral tolerance. Indeed, the data presented herein provides the bases for a method for the generation of adaptive T$^{reg}$ in vitro, and implicates retinoic acid as a potential mediator of gut tolerance in vivo. Moreover, while gut homing is exemplified, T$^{reg}$ of this invention also home to all other organs and thus can be employed to treat autoimmune diseases that are systemic (e.g., Lupus or others) or organ-specific (e.g., Multiple sclerosis or others).

Accordingly, the present invention is an isolated population of retinoic acid-induced adaptive regulatory T cells and a method for producing the same. "Isolated" as used herein signifies that the cells are placed into conditions other than their natural environment and are substantially free of other cell types or are co-cultured with other defined cell types to support viability. In this regard, the effector T cells of the present invention are approximately 90%, 95%, 97%, 98%, 99% pure or homogeneous to effector T cells.

As used herein, an effector T cell is a sub-group of lymphocytes that are also known in the art as conventional T cells and/or TH$_0$ cells. These cells are involved in activating and directing other immune cells, including determining B cell antibody class switching, activating cytotoxic T cells, and maximizing bactericidal activity of phagocytes such as macrophages. Therefore, as used herein the term effector T cell does not include suppressor T cells, natural killer T cells, or cytotoxic T cells. Effector T cells of the invention express the surface protein CD4 (i.e., CD4+); lack expression of CD25, forkhead family transcription factor FOXP3, and CD103 (i.e., CD25−FoxP3−CD103−); and have a pre-defined role as helper T cells within the immune system. Accordingly, effector T cells are also distinct from professional antigen presenting cells such as dendritic cells, macrophages and B cells. Effector T cells can be isolated as exemplified herein or using any other suitable method employed in the art.

Regulatory T cells are a specialized subpopulation of T cells that act to suppress activation of the immune system and thereby maintain immune system homeostasis and tolerance to self. There are at least two subsets of CD4+ regulatory T cells, namely natural and adaptive, that differ in terms of their development, specificity, mechanism of action and dependence on T-cell receptor and co-stimulatory signaling (Bluestone & Abbas (2003) Nat. Rev. Immunol. 3(3):253-7). Whereas natural regulatory T cells are generated as a separate lineage in the thymus, adaptive regulatory T cells originate from peripheral CD4+CD45RO+CD25−Foxp3− T cells (Vukmanovic-Stejic, et al. (2006) J. Clin. Invest. 116(9):2423-2433). Adaptive T regulatory cells produced in accordance with the method of the invention are CD4⁺CD25⁺Foxp3⁺; and express the integrin α4β₇, the chemokine receptor CCR9, and the integrin CD103 thereby exhibiting gut-homing capabilities.

In accordance with the method of the invention, adaptive regulatory T cells are produced from effector T cells using a retinoic acid. Retinoic acids of use in accordance with this method include, but are not limited to, all-trans retinoic acid, 13-cis isomer, 11-cis-retinoic acid, 9-cis-retinoic acid, as well as derivatives thereof (e.g., 4-hydroxy-9-cis-retinoic acid and 4-keto-9-cis-retinoic acid, see U.S. Pat. No. 7,056,954) and synthetic retinoic acid antagonists and agonist. In particular embodiments, the retinoic acid employed is all-trans retinoic acid. The amount of retinoic acid needed to produce an adaptive regulatory T cell from an effector T cell can be based upon the analysis disclosed herein or via routine experimentation. For example, amounts of retinoic acid employed can range from 1 pM to 1 M. More desirably, the amount of retinoic acid employed is between 100 pM and 100 nM.

In addition to natural retinoic acid antagonists and agonist, synthetic retinoic acid antagonists and agonists are also embraced by the present invention, particularly for in vivo manipulation of T$^{reg}$ function. Exemplary retinoic acid antagonists include, but are not limited to, Ro 41-5253, Ro 46-5471, Ro 46-8515, Ro 46-5471, AGN 194310, SR11335, SR11330 and SR11334. Exemplary retinoic acid agonists include, but are not limited to, Ro 13-7410, Ro 19-0645, and N-retinoyl-D-glucosamine.

In addition to retinoic acid, particular embodiments embrace simultaneously or consecutively contacting the effector T cells with a regulatory T cell differentiation composition to promote differentiation of the effector T cells to regulatory T cells. In certain embodiments, the differentiation composition includes one or more of a costimulatory agent, a second regulatory T cell stimulatory agent, or an agent that generally promotes the survival and/or growth of T cells. Costimulatory agents include, e.g., an antibody or ligand specific for a TCR costimulator, such as CD28, CD3 or GITR. In particular embodiments, the costimulatory agent is an agonist antibody or binding protein, such as an agonist antibody or protein which binds to CD28 or CD3. Second regulatory T cell stimulatory agents of use in accordance with the present invention include, e.g., transforming growth factor beta (TGFβ), granulocyte colony stimulating factor, interleukins such as IL-2, IL-6, IL-7, IL-13, and IL-15, and hepatocyte growth factor (HGF). In one embodiment, the second stimulating agent is TGFβ. In another embodiment, the second stimulating agent is a cytokine, such as an interleukin, e.g., IL-2. In a further embodiment, the second stimulating agent is a combination of TGFβ and IL-2.

Regulatory T cells are useful in that they exhibit a bystander effect, e.g., suppressing immune responses in other cells exposed to the same or unrelated antigen. Thus, administration of regulatory T cells can suppress the induction of a response upon stimulation or exposure of antigen to these other cells. This property is important in the context of, e.g., suppression of response to transplantation antigens. See, e.g., Koenen & Joosten (2006) Hum. Immunol. 67(9):665-75. If regulatory T cells specific for the donor antigens are available and administered to a recipient, the tissue rejection response can be suppressed. Conversely, in a bone marrow transplant, the graft immune response to host antigens can be suppressed. Because regulatory T cells induce and maintain immune tolerance and have the capacity to facilitate antigen-specific long-term graft survival successfully in animals receiving allogeneic organ transplants (Long & Wood (2007) Front Biosci. 12:4042-9), adaptive regulatory T cells of the present invention find application in treating autoimmune diseases (e.g., inflammatory bowel disease, rheumatoid arthritis, multiple sclerosis, and diabetes) and facilitating transplantation tolerance. Alternatively, if sufficient adaptive regulatory T cells can be produced, then sufficient numbers of antigen-specific regulatory T cells will be present in that population, and upon transfer can ameliorate a wide spectrum of disease conditions, like graft rejection or autoimmunity.

Thus, in accordance with particular embodiments, the effector T cells of the present invention are further contacted with an autoantigen-specific regulatory T cell stimulatory composition to promote the survival, growth, and/or expansion of autoantigen-specific regulatory T cells that express T cell receptor(s) that recognize a desired autoantigen. Preferred stimulatory compositions stimulate the T cell by antigen-specific binding and activating the T cell receptor complex. A variety of antigen-specific TCR-binding reagents can be used, including cross-linked peptide-bound MHC molecules, antibodies, and mimetics. In one embodiment, the stimulatory compositions include an MHC class II/autoantigenic peptide complex, particularly an aggregate of such MHC/peptide complexes. These complexes contain at least the extracellular peptide binding domain of an MHC class II molecule in which is functionally bound an autoantigenic peptide. Examples of such complexes include those disclosed by Freed, et al. ((2000) J. Immunol. 164:4697-4705) for Lupus erythematosus; Kuwana, et al. ((1998) J. Clin. Invest. 102:1393-402) for Thrombocytopenic purpura; Ettinger & Kwok ((1998) J. Immunol. 160:2365-73) for Type I diabetes mellitus; and Kirshner, et al. ((1996) Scand. J. Immunol. 44:512-21) for Myasthenia gravis. The complexes can be in solution or suspension or immobilized on a substrate, such as presented on the surface of a cell, particularly an APC. Numerous applicable methods are known in the art for generating functional MHC class II/peptide complexes, such as may be found in literature.

In one embodiment, the autoantigenic peptide is a peptide of the naturally occurring autoantigen that is capable of complexing with an MHC class II molecule. Protocols for using autoantigen peptides to stimulate regulatory T cells include the use of autoantigen-specific MHC-peptide tetramers, peptide-pulsed DCs (Yamazaki, et al. (2003) J. Exp. Med. 198: 235-47) or artificial APCs (Maus, et al. (2002) Nat. Biotechnol. 20:143-8).

In certain embodiments, one or more components of the differentiation composition or stimulatory composition are immobilized on a substrate, such as a cell or bead. Cells suitable for use as substrates include artificial antigen-presenting cells (AAPCs) (Kim, et al. (2004) Nat. Biotechnol. 22(4):403-10; Thomas, et al. (2002) Clin. Immunol. 105(3): 259-72). Beads can be plastic, glass, or any other suitable material (e.g., paramagnetic beads), typically in the 1-20 micron range.

Optimal concentrations of each component of the differentiation composition, stimulatory composition, culture conditions and duration can be determined based upon examples disclosed herein or empirically using routine experimentation.

The invention also provides compositions containing a population of cells wherein at least 50% of said cells of said composition are retinoic acid-induced adaptive regulatory T cells, wherein the compositions are made by the methods described herein. In particular embodiments, at least 75%, 85%, 90%, 95%, or 98% of said cells of the composition are adaptive regulatory T cells.

As indicated, adaptive regulatory T cells disclosed herein are introduced into the subject to facilitate transplantation tolerance and prevent, treat or modulate an autoimmune response. In this regard, the instant adaptive regulatory T cells can be used to treat a subject afflicted with a disease or disorder characterized by having an ongoing or recurring autoimmune response, such as Inflammatory Bowel Disease, Lupus erythematosus, Thrombocytopenic purpura, Graves disease, Type I diabetes mellitus, Myasthenia gravis, Pemphigus vulgaris, and Autoimmune hepoatitis. In particular embodiments, treatment or modulation of an autoimmune response involves inhibition or amelioration of the symptoms associated with the autoimmune response in the host, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, such that the host no longer suffers from the condition, or at least the symptoms that characterize the condition.

It is contemplated that treatment can be achieved in vivo or ex vivo. For example, effector T cells can be isolated from a subject, e.g., the subject being treated, and contacted with retinoic acid, with the resulting adaptive regulatory T cells implanted back into the subject. Alternatively, effector T cells can be isolated from a suitable donor. As such, the cells administered to the subject can be either syngeneic (i.e., isologous), allogeneic (i.e., homologous) or xenogeneic (i.e., heterologous) with respect to the subject being treated.

Antigen-specific regulatory T cells are also indicated in infectious diseases in which the pathogenicity of the infections is not a result of the cytopathic effects of the pathogen but rather the tissue damage caused by the immunoinflammatory response to the infectious agent. In diseases, such as hepatitis C or HSV-induced corneal inflammation, regulatory T cell therapy provides a unique opportunity to control viral-induced immunoinflammatory disease (Suvas, et al. (2004) *J. Immunol.* 172:4123-4132). Viruses, such as Coxsackie, are known to cause pancreatitis and have been associated with the development of Type 1 Diabetes. Thus, regulatory T cells that target expressed viral antigens can be used to suppress local tissue damage caused by the infection and reduce the inflammation that incites autoimmune disease development.

In addition, the invention embraces the use of retinoic acid agonists in vivo to increase the frequency of adaptive $T^{reg}$. As such, the administration of retinoic acid agonists to patients with autoimmune disease could be effective in the management of those diseases. On the other hand, the use of retinoic acid antagonists may be suitable for use in vivo in patients where enhancement of immunity is desired, for example, in patients having cancer or in patients receiving a cancer vaccine to induce immunity to that cancer.

Effective and optimized dosages and treatment regimes using the adaptive regulatory T cells of the present invention can be determined by the skilled clinician based on clinical experience with existing T-cell infusion therapies, and can be further determined empirically.

A variety of hosts are treatable according to the subject methods. In certain embodiments, such hosts are mammals, wherein the term is used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The invention is described in greater detail by the following non-limiting examples.

EXAMPLE 1

Materials and Methods

Mice. C57BL/6 and $CB6F_1$, mice were purchased from the National Cancer Institute (Bethesda, Md.). C56BL/6 CD40−/− were purchased from the Jackson Laboratory (Bar Harbor, Me.). FoxP3/GFP reporter mice are known in the art (Fontenot, et al. (2005) *Immunity* 22:329-341). FoxP3/GFP mice were bred with TEa CD4+ Tg mice that express a TCR recognizing peptide in the context of MHC class II presented on all APCs from $H-2^b/I-E^+$ strains ($CB6F_1$), and were bred onto the OTII TCR-Tg mice as well (Quezada, et al. (2005) *J. Immunol.* 175:771-779; Grubin, et al. (1997) *Immunity* 7:197-208). All animals were maintained in a pathogen-free facility.

Cell Preparation. B cells and dendritic cells (DCs) were harvested from the spleens, and CD4+FoxP3− cells were isolated from spleens, peripheral and mesenteric lymph nodes. For B cell and T cells, single-cell suspensions were generated by crushing organs by sterile slides, and purified using by positive selection using either αCD4 or αCD19 labeled magnetic beads (Miltenyi Biotech, Auburn, Calif.). T cells were further purified by FACS-sorting of the CD4FoxP3/GFP− fraction, with purity always exceeding 99% (BD FACSARIA; BD Biosciences, San Jose, Calif.). For CD11c+ positive selection, spleens were harvested and incubated at 37° C. in RPMI with 50 μg/ml DNase I (Sigma, St. Louis, Mo.) and 250 μg/ml LIBERASE (Roche, Indianapolis, Ind.) for 1 hour and pushed through a 100 μM filter to create a single-cell suspension, and then purified using αCD11c magnetic beads (Miltenyi Biotech). Cell preps always exceeded 98% in purity. For small intestine lamina propria lymphocyte preparations, intestines were removed and Peyer's Patches were excised and used for further analysis. The intestines were washed with cold phosphate-buffered saline (PBS), split open, and cut into 1-cm pieces. After a 30-minute incubation in R0 to release the intestinal epithelial lymphocytes (IELs), intestines were vortexed, filtered using a 100 μM filter and washed extensively. Intestines were then digested for 2 hours using 50 μg/ml DNase I (Sigma) and 250 μg/ml LIBERASE (Roche), whereupon they were pushed through a 100 μM filter. The cellular suspension was centrifuged and suspended in 40% PERCOLL, and overlaid on 60% PERCOLL. The PERCOLL gradient was spun at 400 g at room temperature for 25 minutes with no brake, with the buffy (lymphocyte) coat removed for further use. As indicated, APCs were pulsed with ISQ peptide at 10 μg/ml for 1 hour in c-RPMI in six-well plates at a concentration of $10 \times 10^6$ cells/ml, and were then washed, counted, and used.

Cell Culture Reagents. Cells were cultured in RPMI media supplemented with 10% FBS (ATLANTA Biologicals, Lawrenceville, Ga.), HEPES, 50 μM β-mercaptoethanol and Penicillin/Streptomycin/L-Glutamine. LPS was purchased from Sigma. αCD40 (clone FGK-45), αCD154 (clone MR1), αCD28 (clone PV-1), and αCD3 (clone 2C11) were purchased from Bioexpress (West Lebanon, N.H.). For 96-well plate cultures, 200,000 cells in APC/T cell co-cultures (1:1 ratio) in round-bottomed plates or 100,000 T cells in flat-bottomed plates were cultured in 200 μl of media. In each experiment, triplicate wells were set up of each experimental condition. For bulk RA-$T^{reg}$ and adaptive $T^{reg}$ cultures, 24-well flat-well plates were used with 100,000 CD4+ Foxp3− cells/well in 1 ml of media. Unless indicated otherwise, T cells were activated with 1 μg/ml αCD28 and 10 μg/ml αCD3 plate-bound antibody in the presence of 20 ng/ml hTGFβ1 (PeproTech, Rocky Hill, N.J.), 100 U hIL-2

(PeproTech) and all-trans retinoic acid (Sigma). For the in vitro suppressor assay, CFSE-labeled CD4+ T cells (50,000) were co-cultured with irradiated T-depleted splenocytes (100,000), αCD3, and indicated numbers of $T^{reg}$ for 4 days (Thornton, et al. (1998) *J. Exp. Med.* 188:287-296; Takahashi, et al. (1998) *Int. Immunol.* 10:1969-1980).

Flow Cytometry. The following antibodies were used: CD11c clone N418, CD25 clone PC61, CD62L clone MEL-14 (BioLegend, San Diego, Calif.); B220 clone 6B2, CD4 clone L3T4, α4β7 clone DATK32 (BD Pharmingen, San Diego, Calif.); CCR9 clone #242503 (R&D Systems, Minneapolis, Minn.); CD103 clone 2E7, Foxp3 intracellular staining kit (eBioscience, San Diego, Calif.). For CFSE dye dilution, cells were labeled with 5 μM CFSE (Molecular Probes, INVITROGEN, Carlsbad, Calif.). Flow cytometry analysis was performed on a refurbished Becton Dickinson FACSCAN running CELLQUEST software (BD Bioscience), with data analysis performed using FLOWJO (Treestar, Ashland, Oreg.).

Homing Assay. Competitive homing experiments of RA-$T^{reg}$ and adaptive $T^{reg}$ were performed according to established methods (Mora, et al. (2003) supra). In brief, $10\times10^6$ RA-$T^{reg}$ generated from sorted OTII+CD4+Foxp3− cells purified from a OTII+Ly5.2+Foxp3−GFP reporter mouse were mixed with $10\times10^6$ adaptive $T^{reg}$ generated from FACS-sorted OTII+CD4+CD25− cells harvested from an OTII+Ly5.2 mouse and injected intravenously into wild-type C57BL/6 mice. An aliquot was saved to determine the input ratio (IR=[GFP+]input/[GFP−]input). The homing index (HI) was calculated as the ratio of [GFP+]tissue/[GFP−]tissue to IR. Homing indices were tested versus HI=1 using a one-sample Wilcoxon-signed rank test. Significance was set at $P<0.05$.

EXAMPLE 2

Synergistic Enhancement of Foxp3+ T Cells by Retinoic Acid

Figure 2:
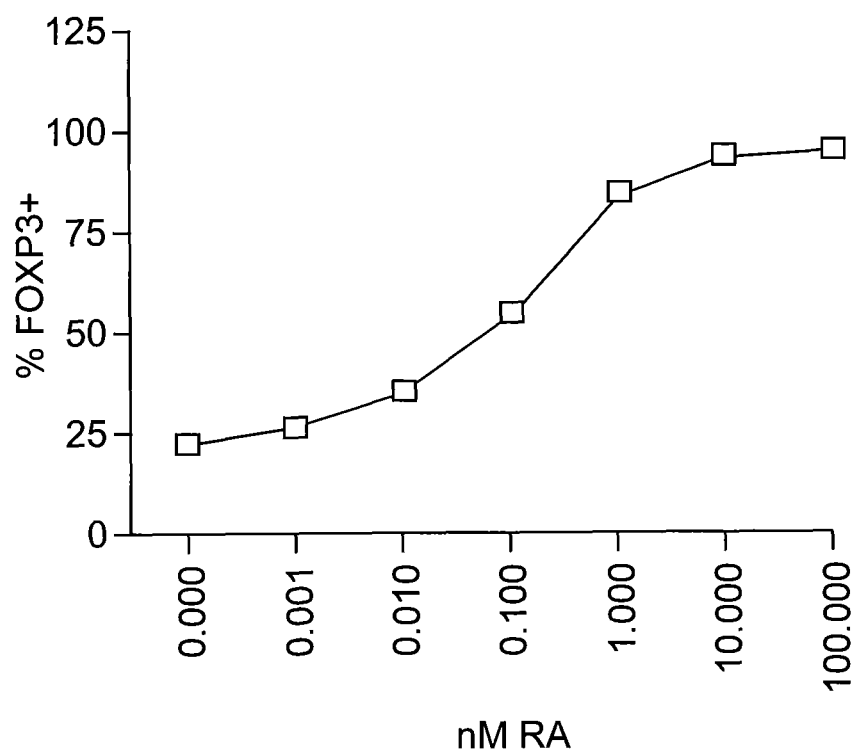
FIG. 2 shows TGF$\beta$-mediated Foxp3/GFP expression as a result of titrating concentrations of retinoic acid (RA). Keeping IL-2 and TGF$\beta$1 constant, retinoic acid was titrated in serial dilutions (100 nM, 10 nM, 1 nM, 100 pM, 10 pM and 1 pM). All experiments shown are representative of 3 repeats.

Retinoic acid has been found to induce α4β7 and CCR9 expression on CD4+ T cells during in vitro activation (Iwata, et al. (2004) supra). As adaptive $T^{reg}$ can be generated from naïve CD4+Foxp3− cells in vitro during stimulation in the presence of TGFβ1 and IL-2, it was determined whether sorted CD4+Foxp3− T cells cultured with TGFβ1, retinoic acid and IL-2 under activating conditions would generate cells with a CD4+Foxp3+α4β7+CCR9+ phenotype. To exclude the presence of Foxp3+ T regulatory cells in the input population, CD4+ Foxp3− cells were sorted from the Foxp3/GFP reporter mouse to >99.9% purity (Fontenot, et al. (2005) *Immunity* 22:329-341). After five days of activation of sorted CD4+FoxP3− T cells by plate-bound αCD3/αCD28 with TGFβ1, IL-2, and retinoic acid, the generation of CD4+FoxP3+α4β7+CCR9+CD103+ T cells was observed. These cells are referred to herein as retinoic acid-induced adaptive regulatory T cells or RA-$T^{regs}$. Concordant with conversion was the induction of CD25, a marker for both T regulatory and activated T cells, and the expression of CD103. CD103 binds E-cadherin expressed on intestinal epithelial cells, is induced by TGFβ1, and has been reported to identify a subset of effector/memory T regulatory cells in vivo that are more potent suppressors then $T^{reg}$ lacking expression of this molecule (Smith, et al. (1994) *Immunity* 1:393-403; Cepek, et al. (1993) *J. Immunol.* 150:3459-3470; Huehn, et al. (2004) *J. Exp. Med.* 199:303-313). A bimodal expression of L-selectin (CD62L) was seen by the Foxp3+ population, with loss of expression correlating with CCR9 induction. This data shows that under these culture conditions, a population bearing the phenotype of a gut-homing adaptive $T^{reg}$ population was generated. In addition, a >90% conversion rate of CD4+FoxP3− to CD4+FoxP3+ T cells was observed in the presence of retinoic acid, compared to 10-30% in its absence. Thus, retinoic acid greatly enhanced the frequency of TGFβ1-induced Foxp3+T cells. To further analyze this synergy, CD4+Foxp3− T cells were activated in the presence of titrated TGFβ1 concentrations with constant concentrations of retinoic acid and IL-2. Retinoic acid enhanced conversion throughout the titration, although retinoic acid, by itself, did not induce conversion. This indicates that conversion was dependent on TGFβ1 (FIG. 1). Similar results were found when retinoic acid was titrated against constant TGFβ1 and IL-2 (FIG. 2). These data indicate that retinoic acid potently enhances TGFβ1-dependent Foxp3 induction during CD4+Foxp3− to CD4+Foxp3+ conversion.

The suppressive activity of RA-$T^{reg}$ was measured relative to that of a $T^{reg}$ and freshly harvested natural $T^{reg}$ in an in vitro suppressor assay. The data show that RA-$T^{reg}$ are potent suppressors of T effector cells in vitro.

Figure 3:
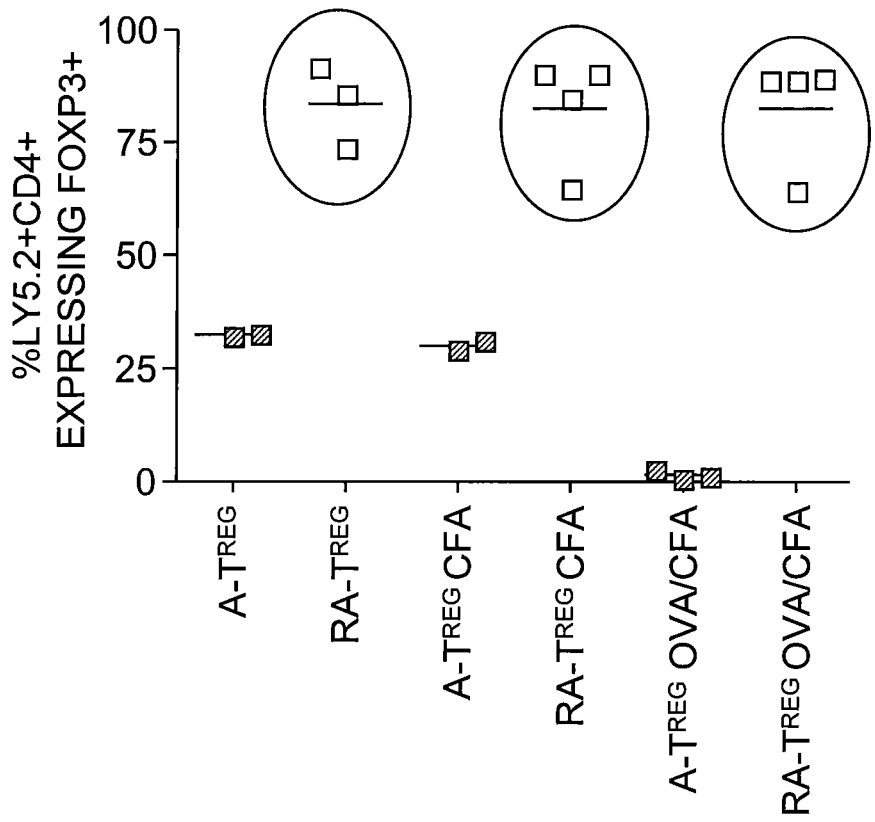
FIG. 3 shows that RA-$T^{reg}$ are suppressive in vitro and refractory to reversion in vivo. The ability of RA-$T^{reg}$ and a$T^{reg}$ to revert in vivo was analyzed by transferring $1.5-2\times 10^6$ FACs-sorted congenically marked OTII+RA-$T^{reg}$ or a$T^{reg}$ generated from a Ly5.2+OTII+Foxp3/GFP mice into Ly5.1+ hosts, who were either left untouched or injected i.p. on the same day with either CFA or 1 mg Ova/CFA as indicated. Donor RA-$T^{reg}$ or a$T^{reg}$ within the spleen were analyzed for Foxp3 expression on day 15 by staining for CD4+Ly5.2+ cells. To examine relative donor T cell expansion 5 days after transfer, the percent of donor OTII+ cells within the recipient splenic CD4+ compartment is shown. RA-$T^{reg}$ data are circled. ***<0.001. Pooled data from n=3.

To examine whether RA-$T^{reg}$ preferentially home to the small intestine, an in vivo competitive homing experiment was conducted (Mora, et al. (2003) supra; Mora, et al. (2005) supra). RA-$T^{reg}$ cells were generated in vitro from a Ly5.2+ Foxp3/GFP reporter mouse, and were thus GFP+Ly5.2+. Adaptive $T^{reg}$ were generated from CD4+CD25− cells sorted from a Ly5.2+ mouse that did not contain the Foxp3/GFP knock-in allele. It was found that CD4+CD25− cells were >99% Foxp3− when examined ex vivo, thus sorting CD4+ CD25− cells eliminates CD4+Foxp3+ contamination prior to inducing conversion. These RA-$T^{reg}$ and adaptive $T^{reg}$ were mixed at a 1:1 ratio and injected intravenously into donor Ly5.1+ mice, and various organs analyzed for donor cells after 18 hours. After at least 18 hours, there was no observed in vivo reversion of CD4+Foxp3+ RA-$T^{reg}$ back to a CD4+Foxp3− phenotype, which would skew the input to output ratios (FIG. 3). As expected from their phenotype, the RA-$T^{reg}$ cells preferentially homed to the small intestine lamina propria, and were in the minority compared to adaptive $T^{reg}$ in the peripheral lymph node, blood, spleen, and lung (Table 1).

TABLE 1

| Location | Homing Index | SEM |
|---|---|---|
| Peripheral lymph node | 0.96 | 0.13 |
| Spleen | 0.96 | 0.08 |
| Blood | 0.56 | 0.05* |
| Lung | 0.39 | 0.02*** |
| Mesenteric lymph nodes | 1.86 | 0.10* |
| Peyer's patches | 3.46 | 0.33* |
| Lamina propria | 12.27 | 0.77** |

Representative of two independent experiments.
Homing index (HI): ([GFP+]tissue/[GFP−]tissue:[GFP+]input/[GFP−]input).
*P < 0.05,
**P < 0.01,
***<0.001 compared with HI = 1.

There was also a significant increase of RA-$T^{reg}$ in the mesenteric lymph nodes and the Peyer's Patches compared to other organs. Collectively, these data show that CD4+Foxp3+ cells with a gut-homing phenotype can be generated from CD4+Foxp3−T cells in vitro, and this cell population preferentially homes to the small intestine in vivo.

EXAMPLE 3

Figure 4A:
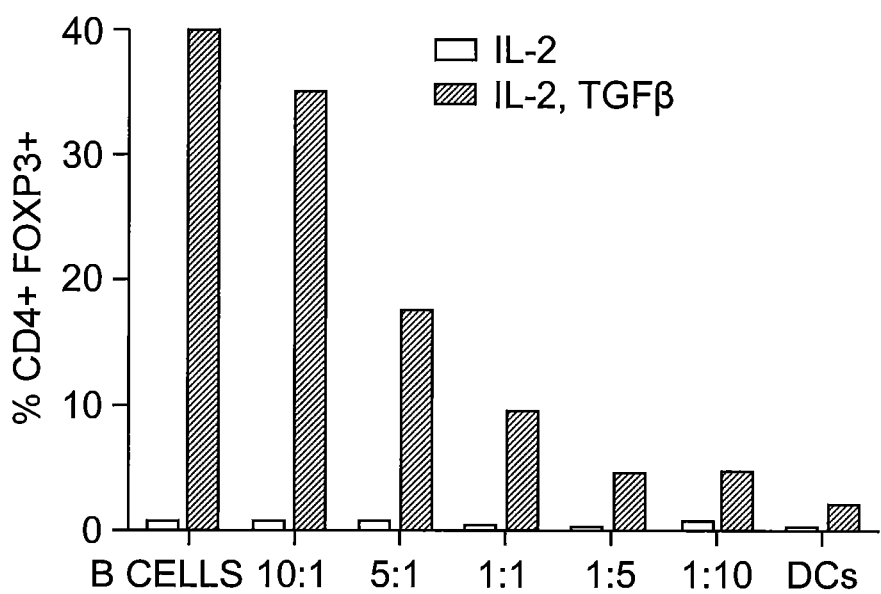
FIG. 4A, either B cells alone, DCs alone, or B cells mixed with DCs at ratios of 10:1, 5:1, 1:1, 1:5, 1:10 at a constant APC/T cell ratio of 1 were cultured with the indicated cytokines, with CD4+ T cells analyzed for Foxp3/GFP expression.

Retinoic Acid Enhances the Ability of DCs to Induce TGFβ1-Mediated Foxp3 Induction in the Face of Co-Stimulation To investigate the capacity of different APC subsets to induce adaptive $T^{reg}$ generation in vitro, peptide-pulsed splenic CD19+ B cells and CD11c+ DCs were analyzed for their ability to induce TGFβ1-driven adaptive $T^{reg}$ conversion from CD4+OTII+Foxp3− cells. A difference was observed between these two APC subsets to mediate conversion: B cells repeatedly induced conversion at rates between 40-60%, with DCs inducing conversion at the substantially lower rate of 0-14%, as previously reported (Kim, et al. (2006) *Immunol. Rev.* 212:86-98). Within each experiment, there was consistently a difference of at least 30% conversion between DCs and B cells. These results were repeated using a different transgenic system to verify that these data are not unique to CD4+OTII+ transgenic T cells. Using a TCR Tg CD4+ (TEa) with specificity to a major alloantigen (Eα in the context of I-$A^b$) expressed by F1 (H-$2^{bxd}$) APCs, the same rate of conversion was induced by F1 B cells as those observed by the OTII system, with F1 DCs consistently less effective then B cells at inducing the conversion. The ratio of B cells to DCs was titrated in a B cell/DC/OTII co-culture to examine whether DCs can override the conversion imparted by B cells on the T cells or vice versa. It was found that the percent of conversion correlated to the number of B cells available for peptide presentation, indicating that conversion directly related to the number of B cells available for antigen presentation and that neither APC subset could override the other (FIG. 4A).

It was contemplated that the co-stimulatory capacity of APCs is inversely correlated with the generation of adaptive $T^{reg}$. In this context, it was determined whether B cell activation and the acquisition of heightened co-stimulation impaired the ability of B cells to induce conversion. When CD19+ B cells were pre-activated for 48 hours by either LPS or agonistic-αCD40 supplemented with IL-4 and then used as APCs, B cell-mediated conversion was impaired. The activation of both B cells and DCs through CD40 engagement by its ligand, CD154, can be inhibited using a αCD154 blocking antibody, with suppressed co-stimulatory molecule expression by B cells and DCs the consequence. When CD40/CD154 interactions were blocked by αCD154 antibody, DCs were then able to mediate conversion. Similar results were observed using CD40 knockout DCs.

Figure 4B:
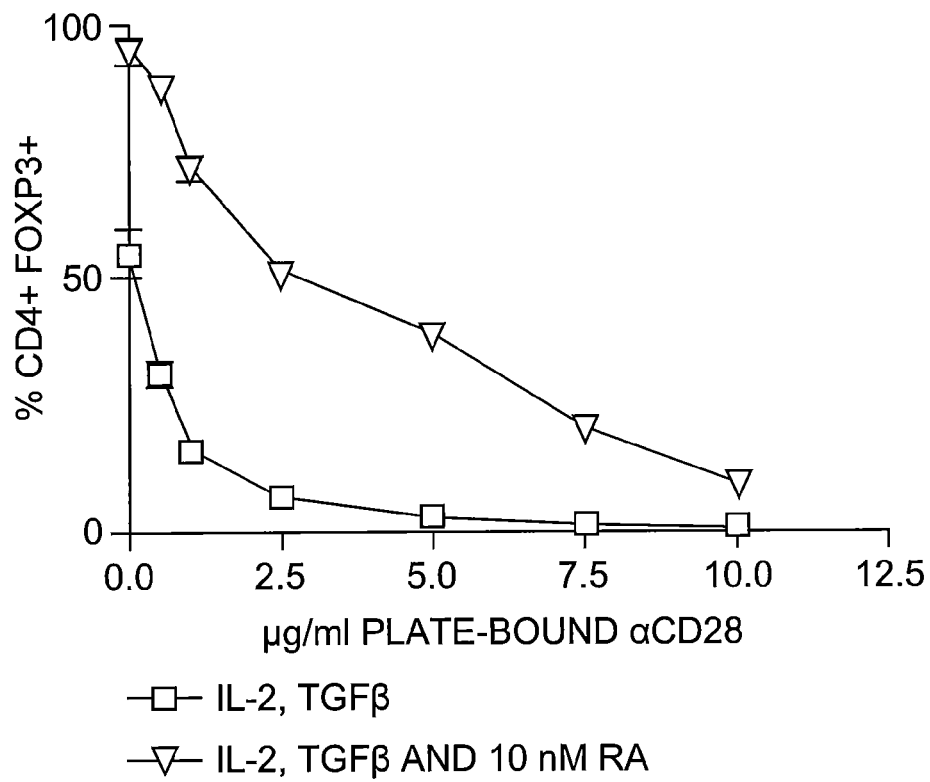
FIG. 4B, CD4+ T cells were activated using plate-bound 10 µg/ml αCD3 and titrating concentrations of αCD28 with IL-2 and TGFβ1, +/− RA as indicated, with Foxp3/GFP expression plotted as a function of plate-bound αCD28 concentration. Each experiment shown is representative of at least 3 repeats.

When the magnitude of co-stimulation was varied in an in vitro assay in which plate-bound agonistic αCD28 was titrated against saturating concentrations of plate-bound αCD3, it was observed that αCD28 concentration had an inverse relationship with adaptive $T^{reg}$ generation. Optimal conversion consistently occurred at low doses of αCD28 concentration, at approximately 1 µg/ml and below. At saturating, or 10 µg/ml, of αCD28, no conversion was observed (FIG. 4B). Taken together, these data show that high levels of co-stimulation, such as that observed on splenic CD11c+ DCs, impairs TGFβ1-driven adaptive $T^{reg}$ generation from CD4+Foxp3− cells, and little to no co-stimulation, such as levels present on resting B cells, are ideal for inducing conversion.

The addition of retinoic acid to the co-stimulation assay led to enhanced conversion across all concentrations of αCD28 (FIG. 4B). Importantly, even at saturating concentrations of αCD28, conversion was observed, indicating that retinoic acid allows Foxp3 induction to occur even during the highest levels of co-stimulation. It was found that αCD28 concentration had an inverse relationship with a$T^{reg}$ generation, with optimal conversion occurring at αCD28 concentrations of 1 µg/ml and below. At saturating, or 10 µg/ml of αCD28, no conversion was observed. Taken in sum, these data show that high levels of CD80/86 co-stimulation, such as those observed on splenic CD11c+ DCs, is not optimal for TGFβ1-driven Foxp3 induction and a$T^{reg}$ generation while inducing maximal expansion of T cells.

The observation that RA-$T^{reg}$ can be induced in the presence of high levels of co-stimulation indicated that retinoic acid enhances the induction of Foxp3 via interrupting co-stimulation and inhibiting T cell proliferation. To visualize whether this occurs, CFSE-labeled CD4+CD25− cells were activated in the presence and absence of retinoic acid to observe TGFβ1-driven conversion. One nM of retinoic acid was used in the cultures as this concentration has been reported to drive T cell differentiation without inhibiting proliferation, and this concentration also enhances Foxp3 (FIG. 2). In contrast, high doses of retinoic acid (30-100 nM) suppress T cell proliferation, while doses below 5 nM do not inhibit proliferation (Racke, et al. (1995) *J. Immunol.* 154:450-458). The data shows that 1 nM retinoic acid does not suppress T cell proliferation as indicated by CFSE dye dilution profile. In concordance with its known T-cell suppressive character, the addition of TGFβ to cultures slowed T cell division, and yielded a Foxp3+ population. The addition of retinoic acid to the TGFβ1 and IL-2 cultures generated a substantially greater number of Foxp3+ cells throughout all peaks of cell division, with no impediment in cell division observed. This indicates that retinoic acid enhances Foxp3 expression through a mechanism independent of impeding co-stimulation. Further supporting this finding is that retinoic acid enhances TGFβ1-mediated Foxp3 expression in the absence of co-stimulation and just the presence of an agonistic TCR signal (FIG. 4B). This data shows that retinoic acid enhances Foxp3 induction through a mechanism independent of dampening T cell co-stimulation and proliferation, and that retinoic acid uncouples co-stimulation from interfering with Foxp3 induction.

EXAMPLE 4

Retinoic Acid Yields a Net Increase of $T^{reg}$ with Suppressive Activity

Figure 5:
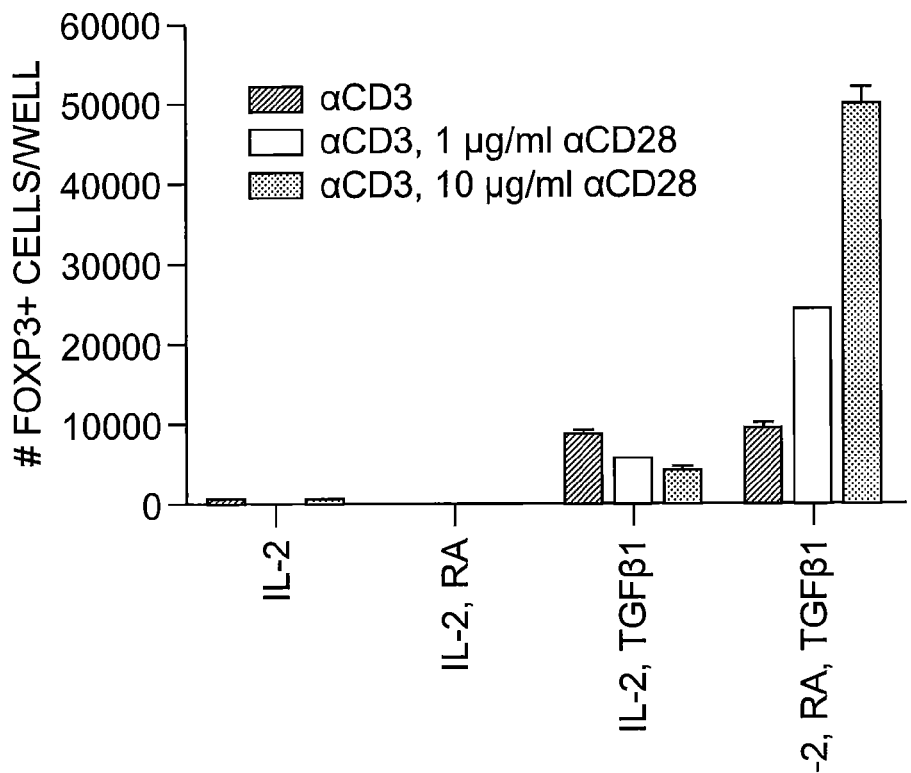
FIG. 5 shows that retinoic acid enhances the total cell number of RA-T$^{reg}$. Sorted T cells, from a Foxp3/GFP reporter mouse, were cultured under the indicated conditions with total cell numbers/well counted, percent of cells/well expressing Foxp3/GFP determined, and the total number of Foxp3/GFP expressing cells/well shown. Representative experiments of at least n=3.

To determine whether the addition of retinoic acid to adaptive $T^{reg}$ cultures results in a net increase of Foxp3+ cells, the total numbers of adaptive $T^{reg}$ and RA-$T^{reg}$ present after five days of culture and generated under different activating and culture conditions were measured (FIG. 5). The addition of retinoic acid greatly enhanced the total number of TGFβ1-dependent Foxp3+ cells in conditions of high, low and no co-stimulation (FIG. 5), compared to culture conditions in the absence of retinoic acid. In sum, retinoic acid greatly enhances both the conversion and total numbers of Foxp3+ expressing T cells through a mechanism independent of co-stimulation inhibition.

EXAMPLE 5

$CD8a^+$DCs Induce Conversion of Antigen-Specific $T^{reg}$ that is Retinoic Acid-Dependent The role of retinoic acid and the efficacy of different DC subsets in the conversion of effector T cells to Foxp3+ cells were also evaluated. To determine the influence of DC subsets on aT$^{reg}$ differentiation, purified CD8α$^+$ or CD8α$^-$ CD11c$^{high}$ DCs were tested for their capacity to induce Foxp3 expression in naïve CD4$^+$ OTII TCR Foxp3GFP$^-$ T cells. Upon in vitro culture for 5 days with either the CD8α$^+$ or CD8α$^-$ CD11c$^{high}$ splenic DCs in the presence of antigenic OVA peptide and TGFβ, CD8α$^+$ DCs were superior inducers of Foxp3 expression in the presence of TGFβ when compared to CD8α$^-$ DCs. To compare the ability for each DC subset to induce clonal expansion, the number of OTII cells was quantified at the end of the assay. Although CD8α$^-$ DCs induced modestly better proliferation of total CD4$^+$ T cells, the number of induced Foxp3$^+$ cells was still greater with the CD8α$^+$ DC culture. To evaluate if retinoic acid was involved in the DC-induced conversion, the pan RAR inhibitor, LE540 was used at non-toxic concentrations. Induction of Foxp3 was inhibited by this intervention. Hence, retinoic acid appears critical for DC-induced conversion. Thus, it is contemplated that peripheral (not only mucosal DCs) induces T$^{eff}$->T$^{reg}$ differentiation in a retinoic acid-dependent manner.

EXAMPLE 6

Retinoic Acid Receptor (RAR)α is Critical in Retinoic Acid-induced aT$^{reg}$ Differentiation The data herein shows that retinoic acid acts directly on T cells to enhance their differentiation to Foxp3$^+$ T cells. To identify the RAR involved in retinoic acid-induced differentiation, RAR selective agonists were tested for their ability to induce Foxp3$^+$ T cells. The results of this analysis indicated that only the RARα agonist exerted a significant impact on the expression of Foxp3.

Given the overwhelming impact of RAR (on T$^{reg}$) and ROR (RORγt on Th17) on T cell differentiation, these receptors could play a decisive role in the fate of T cells. As such, a comprehensive analysis of RAR and RXR (the two receptors that govern responsiveness to retinoic acid) expression and function was carried out. RT-PCR analysis indicated that expression of the three RARs along with RXR were detected at low levels in freshly isolated CD4$^+$, CD25$^-$ and CD4$^+$, CD25$^+$ T cells. Expression of RARα and RXR was increased in aT$^{reg}$, and expression of RAR α, β, and γ, RXRα, and RXRβ was increased in retinoic acid-treated T cells (Kang, et al. (1987) *J. Immunology* 139:1154-1160). Analysis of receptor expression by western blot analysis, and additional studies by RT-PCR analysis are carried out to determine the contribution that this family of receptors makes to T cell differentiation. Hence, from the B6 Foxp3-GFP mice, sort-purified nT$^{reg}$ (Foxp3$^+$), T$^{eff}$ (Foxp3$^-$), aT$^{reg}$ (Foxp3$^+$ from culture with αCD3, IL2 and TGFβ) and RA-T$^{reg}$ (Foxp3$^+$ from culture with αCD3, retinoic acid, IL2 and TGFβ) are used for RT-PCR analysis for the above noted RAR and RXR, and for western blot analysis using commercially available antibodies. The presence or absence of specific receptors provides guidance for functional studies using RAR and RXR agonists and antagonists.

Recognizing the mechanistic involvement of RAR and RXR heterodimers in regulating this maturation program, a panel of suitable RAR selective agonists (and non-classical retinoids) can be employed. Their use to identify functionally significant receptor complexes are important because: inhibitor/agonist studies can identify functionally significant receptors involved in T$^{eff}$->T$^{reg}$ conversion; knowing the relevant receptors, the appropriate RARs/RXRs can be genetically engineered in vivo in T cells to able to manipulate their response to retinoic acid, thereby specifically controlling retinoic acid signaling to the T cell with minimal disruption of other important signaling pathways and without effects in the non-T cell compartment; and use of the relevant inhibitors/agonists in vivo facilitates the study of their impact on tolerance.

Given the data herein, retinoid receptor-specific agonists and antagonists such as tamibarotene, AM580 (RARα agonists), AC55649 (RARβ agonist), CD437 (RARγ agonist), a mixed RAR-RXR agonist (bexarotene with RXR>RAR activity), pure RXR agonists (NRX4204 and LGD-100268), a pan-RAR antagonists (LE540, LGD-100815) and a proapoptotic retinoid (fenretinide) are used as molecular pharmacologic tools to mechanistically probe which of the classical (RARs) or non-classical (RXRs) retinoid receptors confers retinoid response in the maturation of T$^{eff}$->T$^{reg}$ lymphocytes, both in vivo and in vitro. As indicated by results obtained herein, the in vivo effects of regulating T$^{eff}$->T$^{reg}$ in mice is determined using these agents as pharmacological tools. Briefly, the RAR and RXR agonists (used in the sub- to μM range to retain specificity) are tested with sort-purified, Foxp3$^-$ when cultured with TGFβ, IL2 and αCD3. Expression of Foxp3, CCR9, and α4β37 is tested, as is their suppressor cell activities, in standard suppressor assays. See, e.g., Gondek, et al. (2005) *J. Immunol.* 174:1783-6. This is to assure that a single agonist can induce all of the cellular responses associated with retinoic acid. RAR selective antagonists are also used to block the effects of retinoic acid to confirm the activities seen with the agonists. These in vitro findings are then correlated with in vivo studies on the utility of these agents to trigger or interfere with T$^{eff}$->T$^{reg}$ in vivo.

Indeed, using receptor specific agonists and antagonists, the RAR/RXR heterocomplexes involved in the induction of Foxp3 were identified. Using a RXRα agonist, (4204 from NuRx Pharmaceuticals, Irvine, Calif.) it was shown that RXRα is involved with the induction of Foxp3. As such, T cells of a line of mice in which the RXRα gene is conditionally mutated by introduction of loxP sites into introns flanking exon 4 of the RXRα gene are anticipated to be unresponsive to retinoic acid signaling and conversion in vivo.

The in vitro data provided herein implicates RARα in T$^{eff}$->T$^{reg}$ differentiation. To decisively ascertain the role of RA in T$^{eff}$->T$^{reg}$ differentiation in vivo, selective interference of RARα signaling in the CD4 compartment is critical. Overexpression of the dominant-negative RARα has been widely used to interfere with retinoic acid signaling in vivo in a tissue-restricted fashion (Yang, et al. (2003) *Endocrinology* 144:3004-11; Attar, et al. (1997) *Mol. Endocrinol.* 11:792-800; Damm, et al. (1993) *Proc. Natl. Acad. Sci. USA* 90:2989-93). To selectively restrict retinoic acid signaling within the CD4$^+$ T cell compartment, the following vectors are used to engineer mice that over-express the dominant-negative RARα in the CD4 compartment: A CD4-transgene containing 350-bp minimal enhancer, 500-kb promoter, untranslated exon I, intron I (8.6 kb) and part of Exon II of the murine CD4 gene linked to the SV40 polyadenylation site (Sawada, et al. (1994) *Cell* 77:917-29) and retroviral vector LRARa403SN containing a dominant-negative form of RARα (Tsai, et al. (1992) Tohoku *J. Exp. Med.* 166:289-96). The RARα dominant-negative protein is expressed as an N- or C-terminal fusion protein with the red fluorescent protein gene (tomato, RFP) to facilitate the detection of CD4$^+$ T cells expressing the dominant-negative (DN) protein. C-terminal fusion of RAR receptors which retain functional activities have been described (Maruvada, et al. (2003) *J. Biol. Chem.* 278:12425-32; Minucci, et al. (2002) *Blood* 100:2989-95). The DN-RARα (RARα403; contained in vector LRARa$_{403}$S, GenBank NM_000964) is initially subcloned into retroviral vectors allowing for RFP expression at the C-terminus of the expressed fusion protein. Retroviral overexpression of DN- RARα-RFP in the RAR reporter cell line (F9-RARE-LacZ cell line (Wagner (1997) *Methods Enzymol.* 282:98-107) that is responsive to retinoic acid, and purified CD4+ T cells from the B6-GFP-Foxp3 reporter mice allows for testing the activity of the DN construct. Purified CD4+B6-GFP-Foxp3− T cells are grown with αCD3 and IL2 (for three days) and retrovirally-infected, then switched to TGFβ and retinoic acid. Under these conditions, cells that are red (expressing the DN-RARα) should not be able to turn green (indicative of Foxp3 expression) in response to retinoic acid. Using the C-terminal construct, transgenic mice are produced by pronuclear injections. Positive founder mice are identified by the expression of RFP in the CD4+ T cells in peripheral blood. Functional assessment of the DN-RARα is confirmed by the inability of purified CD4+ T cells to express Foxp3, CCR9 and α4β7 when cultured in vivo with αCD3, IL2, TGFβ and graded doses of retinoic acid. Restricted expression within the CD4 compartment is expected, which will be ascertained by RFP expression.

Indeed, mice were created in which retinoic acid signaling to the CD4 compartment was selectively impaired. Transgenic (Tg) MMTV-DN (dominant-negative) RARα mice, which 10 express DN-RARα in the CD4 compartment were generated for use in in vivo studies of the effects of retinoic acid on $T^{reg}$ conversion. It was found that the DN-RARα message was expressed in purified CD4+ T cells from these mice and that retinoic acid-induced Foxp3 expression was impaired. As such, mice in which CD4+T cells from the MMTV Tg mice can be transferred into B6 hosts thereby allowing for the evaluation of CD4+$T^{eff}$->$T^{reg}$ conversion in vivo.

In addition, a dominant negative-RARα-Thy1.1 IRES construct was produced in a retroviral vector. This vector was shown to be capable of overexpressing the DN-RARα protein in OTII T cells. When analyzed, the Thy1.1+OTII cells, but not those infected with control vector, were unresponsive to retinoic acid-induced upregulation of Foxp3. Expression of the DN-RARα completely blocked the upregulation of Foxp3, but the control vector was without effect. Given these results, this IRES construct was introduced into a CD4 transgenic vector to selectively restrict retinoic acid signaling within the CD4+ T cell compartment. In addition, CD4+ TEa Tg T cells can be infected to prevent retinoic acid-induced conversion in a transplant tolerance model.

Having confirmed that the DN-RARα impairs retinoic acid-induced $T^{eff}$->$T^{reg}$ conversion, a more extensive analysis of the functional activity of these cells is performed. A severe impact on T cell ontogeny is not expected, as intense Vitamin A deficiency has a modest impact on T cell ontogeny (Smith, et al. (1987) *J. Nutr.* 117:857-65). Thus, wild-type and DN-RARα T cells are placed in culture in Th1 (IFNγ, anti-αIL4), Th2 (IL4, αIFNγ), TH17 (TGFβ and IL6) and $T^{reg}$ (TGFβ, +/− retinoic acid). Luminex analysis is used to evaluate cytokine production (IL2, IL4, IFNγ, TGFβ, IL5, IL17) following skewing conditions. The DN-RARα construct may or may not heighten Th17 skewing in the absence of exogenous retinoic acid. It is expected that DN-RARα should not alter Th1 or Th2 skewing.

Use of the RXR agonists indicates the involvement of RXR in $T^{eff}$->$T^{reg}$ conversion. Mice in which RXRα has been floxed are known in the art (Wan, et al. (2000) *Mol. Cell Biol.* 20:4436-44). It has been shown that crossing of RXRα$^{FLOX}$ with lck-cre resulted in mice in which the T cell compartment was modestly altered with regard to cell numbers and phenotype, but biased to a Th1 phenotype. These findings are consistent with the repeated observations that retinoic acid tilts mature T cells to a Th2 profile (Stephensen, et al. (2007) *Immunology* 121:484-98). Analysis of changes in homing or Foxp3 expression was not evaluated. Thus, RXRα$^{FLOX}$ mice are interbred onto the CD4-cre (JAX Labs) and B6 Foxp3-GFP. As the RXRα are available for receipt, if RXRα is involved in $T^{eff}$->$T^{reg}$, this provides an immediate means to selectively interfere with retinoic acid signaling in T cells and affords a unique opportunity to study the role of retinoic acid in $T^{eff}$->$T^{reg}$ in vivo. The in vitro response of CD4$^{cre}$xRXR$^{FLOX}$ T cells to express Foxp3 in response to graded doses of retinoic acid in the presence of αCD3, TGFβ and IL2 is analyzed. If impairment is observed, then the phenotype and function of the CD4$^{cre}$xRXR$^{FLOX}$ T cells are evaluated, as described for the DN RARα T cells. The CD4-DN RARα and CD4$^{cre}$x RXR$^{FLOX}$ T cells mice can also be exploited in in vivo studies.

EXAMPLE 7

RA-$T^{reg}$ are Committed, Differentiated $T^{reg}$

The analysis conducted herein indicates that RA-$T^{reg}$ are differentiated $T^{reg}$. The designation of RA-$T^{reg}$ as effector or committed $T^{reg}$ is based upon the following. RA-$T^{reg}$ Express CD103. Initial differences in RA-$T^{reg}$ vs a$T^{reg}$ are shown by the expression of CD103, CCR9 and α4β7 on RA-$T^{reg}$ as compared to a$T^{reg}$; retinoic acid induces 72% of the $T^{reg}$ to expression CD103, which has been shown to be expressed on $T^{reg}$ with the highest level of suppressive activity in vivo (Allakhverdi, et al. (2006) *J. Allergy Clin. Immunol.* 118: 1342-9; Leithauser, et al. (2006) *Am. J. Pathol.* 168:1898-909).

Gene Expression Profiling on a$T^{reg}$ vs n$T^{reg}$ vs RA-$T^{reg}$. Transcriptional profiling substantiates differential gene expression in a$T^{reg}$ vs RA-$T^{reg}$. Most notably, in RA-$T^{reg}$ there is a down-regulation of both IL10 and IL9, two suppressive cytokines that have been shown to be important in mediating suppression in some systems (Lu, et al. (2006) *Nature* 442:997-1002). Increased signal for CCR9 in RA-$T^{reg}$ is consistent with increased expression of CCR9 on their cell surface. More extensive transcriptional profiling can be conducted to analyze the differential biology of a$T^{reg}$ vs RA-$T^{reg}$.

a$T^{reg}$ do not Produce IL9 in the presence of Retinoic Acid. Transcriptional profiling showed that RA-$T^{reg}$ had down-regulated the expression of IL9, a cytokine amply produced by a$T^{reg}$. To further validate this data, IL9 production by a$T^{reg}$ and RA-$T^{reg}$ was quantified. This analysis indicated that retinoic acid caused a dose-dependent decrease in the production of IL9 by T cells stimulated with αCD3, IL2 and TGFβ (a$T^{reg}$), confirming the transcriptional profiling data. These data suggest that a$T^{reg}$ and RA-$T^{reg}$ may produce a different array of cytokines.

RA-$T^{reg}$ are Refractory to Reversion in vivo. Retinoic acid is known to induce differentiation in a variety of primary and tumor cell types. As such, it was determined whether RA-$T^{reg}$ cells were more committed to the $T^{reg}$ lineage and less prone to revert to Foxp3− T cells then adaptive $T^{reg}$ from a natural source. To examine the propensity of a$T^{reg}$ and RA-$T^{reg}$ to revert under different in vivo conditions, a$T^{reg}$ and RA-$T^{reg}$ cells were generated from Ly5.2+OTII+Foxp3/GFP reporter mice, sorted to >99.9% FoxP3+ and transferred into Ly5.1+ recipients. Hosts were either un-manipulated, immunized with Ova/CFA, or PBS/CFA (FIG. 3). After fifteen days, the transferred cells were analyzed for Foxp3 expression. Twenty percent of the RA-$T^{reg}$ lost Foxp3 expression under all condition, whereas in un-manipulated, CFA or CFA/OVA, the a$T^{reg}$ reverted from 70->100%. Hence, these data demonstrate that RA-$T^{reg}$ are committed Foxp3+ T cells. Thus, based on gene profiling, differential cytokine expression and their commitment to the expression of Foxp3, RA-T$^{reg}$ are differentiated from aT$^{reg}$.

Having demonstrated that RA-T$^{reg}$ are differentiated, committed, effector T$^{reg}$, the differentiative state of the RA-T$^{reg}$ vs aT$^{reg}$ vs nTreg is defined. This analysis is carried by out analyzing cytokine production. There are few cytokines that define T$^{reg}$. Cytokines that mediate immune suppression by T$^{reg}$ are IL9, IL-10 and TGFβ. All of these cytokines have been shown to be functionally important in either graft tolerance or inflammatory bowel disease (Lu, et al. (2006) *Nature* 442:997-1002; Waldmann, et al. (2006) *Immunol Rev* 212: 301-13; Ohga, et al. (2004) *J. Med. Virol.* 74:449; Schramm, et al. (2004) *Int. Immunol.* 16:1241-1249). It has been shown that IL9 is important in T$^{reg}$-dependent allograft tolerance (Lu, et al. (2006) supra), and is produced by nT$^{reg}$ and aT$^{reg}$, but not RA-T$^{reg}$. IL-35 has also been identified as another T$^{reg}$-derived cytokine involved with suppression (Collison, et al. (2007) *Nature* 450:566-9). Therefore, a more comprehensive evaluation of cytokine production by nT$^{reg}$, aT$^{reg}$ and RA-T$^{reg}$ can be conducted by analyzing the expression of IL2, IL4, IL6, IL9, IL10, IL17, TGFβ (active), TNFα, and IFNγ. This analysis confirms that retinoic acid causes a differential expression in cytokine expression from other T$^{reg}$ preparations.

Suitable leads demonstrating altered gene expression in RA-T$^{reg}$ from other T$^{reg}$ populations are more extensively analyzed by gene expression profiling. Experimental groups include resting and αCD3 (4, 8, 16 hours) activated nTreg, T$^{ef}$, aT$^{reg}$ and RA-T$^{reg}$. Statistical differences are decided based on T-test of expression signals between groups p=<0.05 for statistically different genes or p=>0.05 for genes not different. The results of such analysis demonstrate cytokines, chemokines or CDs that are uniquely expressed by RA-T$^{reg}$ vs aT$^{reg}$ or nT$^{reg}$, and define the differentiative phenotype of the RA-T$^{reg}$.

Multiple lines of evidence indicate that retinoic acid is produced in the graft tolerance system described herein and is functionally essential for sustaining allograft survival. However, it has been shown that retinoic acid shuts down IL-9 synthesis and induces gut homing receptors, which should divert RA-T$^{reg}$ from the skin. Further, the environment of the skin exerts additional regulatory influences over RA-T$^{reg}$. For example, it has been shown that 1,25D (produced in the skin) inhibits the retinoic acid-induced expression of α4β7 and CCR9 (Iwata, et al. (2003) *Int. Immunol.* 15:1017-25). Assuming both retinoic acid and 1,25D are produced in the skin, it is expected that "RA-like" T$^{reg}$ are induced that do not express gut homing receptors, and have upregulated CCR10 so RA-T$^{reg}$ are retained in the skin due to the dominant actions of 1,25D (produced in the skin) to induce the skin retention even in the presence of retinoic acid. Initial studies indicate that over a broad dose range, 1,25D does not interfere with retinoic acid-induced Foxp3 expression nor does it induce Foxp3 expression with αCD3 and TGFβ. Moreover it is expected that 1,25D+RA-T$^{reg}$ will be superlative suppressors of graft rejection due to their homing character and high levels of Foxp3.

EXAMPLE 8

Retinoic Acid and aT$^{reg}$ in Allograft Tolerance

The contribution of retinoic acid to peripheral tolerance was analyzed in models of graft tolerance. To evaluate whether retinoic acid was critical for the conversion of aT$^{reg}$ in vivo, a graft tolerance model was employed that has been shown to be dependent on the infiltration of T$^{reg}$ into the allograft. In this model, the elimination of T$^{reg}$ causes rapid graft loss in mice that are rendered tolerant (Quezada, et al. (2004) *Annu. Rev. Immunol.* 22:307-28; Quezada, et al. (2003) *Blood* 102:1920-6; Gonzalez, et al. (2002) *J. Immunol.* 169:5581-9). In these studies, mice were tolerized to alloantigen using donor alloantigen-bearing leukocytes as an infusion (so-called Donor Specific Transfusion: DST) and αCD154 (CD40L). Following this treatment, mice were grafted with allogeneic skin. αCD154/DST induces long-term tolerance to the donor alloantigen and permits the transplantation of an allogeneic skin graft.

Figure 6:
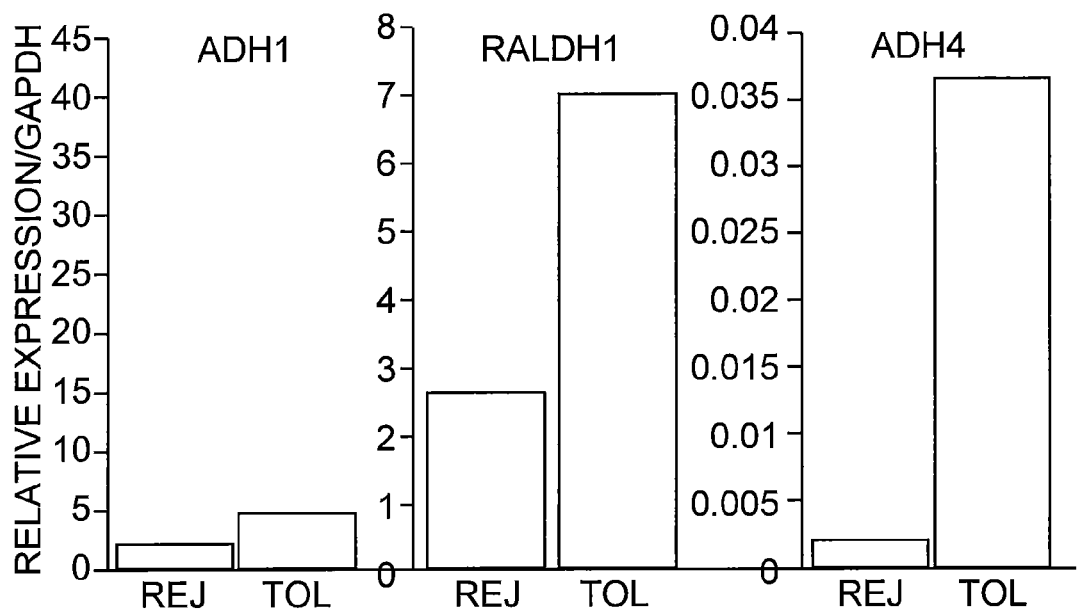
FIG. 6 shows the heightened levels of retinoic acid biosynthetic enzymes in tolerant skin. cDNA was prepared from day 30 tolerant (Tol) and day 7 rejecting (Rej) allogeneic skin grafts. cDNA was prepared and quantitative RT-PCR analysis performed. Results are expressed relative to GAPDH.

RT-PCR Analysis of Enzymes Involved in Retinoic Acid Biosynthesis. Alcohol dehydrogenase (ADH) and retinaldehyde dehydrogenase (RALDH) are two enzymes involved in the biosynthesis of retinoic acid, the later being most critical for the irreversible synthesis of the product, retinoic acid. RT-PCR analysis of day 7 rejecting vs day 30 tolerant skin revealed marked differences in ADH and RALDH expression (FIG. 6).

Expression of RALDH in Tolerant Skin and in Mice that are Vitamin A Deficient. As disclosed herein, mice placed on a Vitamin A deficient diet cannot be tolerized using DST/αCD154 to sustain a skin allograft. It has been reported that Vitamin A deficiency induces squamous metaplasia in the tracheal epithelium and also down-regulates RALDH expression (Bhat, et al. (1998) *Biochem. Cell Biol.* 76:59-62). Accordingly, grafts from day 14 tolerized skin, syngeneic grafts, both on a normal diet, or tolerant grafts from mice on a Vitamin A-deficient diet were prepared and stained with a commercially available, polyclonal αRALDH antibody or isotype control antibody. This analysis showed positive RALDH expression in Day 14 tolerant skin, not in syngeneic grafts and loss of staining in mice that have been on a Vitamin A-deficient diet. This establishes expression of RALDH in tolerant skin and mice on diets were Vitamin A is deficient.

Factors from Tolerant Allografts Enhance T$^{ef}$->T$^{reg}$ Conversion. To determine whether factors produced by tolerant allografts can facilitate the conversion of T$^{ef}$->T$^{reg}$, factors were obtained from syngeneic skin grafts (day 10) or tolerant skin grafts (day 10) by culture of those grafts in media for 1 hour at 37° C. These factor preparations were diluted in assays to measure T$^{ef}$->T$^{reg}$ conversion using αCD3/αCD28 and TGFβ. After 5 days of culture, the cells were assessed for Foxp3 expression. The results of this analysis indicated that factors derived from tolerant allograft, but not syngeneic grafts were potent in inducing the conversion of Foxp3-->Foxp3$^+$ T cells.

DCs Within Tolerant Allografts have Heightened Migratory Capacity. It has been shown that retinoic acid enhances the migration of DCs from tissue to the draining LN (Darmanin, et al. (2007) *J. Immunol.* 179:4616-25). It has been shown that the retinoic acid-matured DCs had an enhanced capacity to migrate through the basement membrane matrix toward the lymphoid chemokines CCL19 and CCL21 due to an increase in MMP production. Thus, it was determined whether enhanced DC migration could be visualized in vivo in tolerant vs syngeneic vs rejecting allografts. To this end, mice were given a syngeneic graft, an allograft or tolerized with αCD154/DST. On day 10, the grafts were painted with a small volume of FITC, such that the surrounding autologous areas were not painted. The following day, the frequency of FITC-DC in the DLN were quantified by flow cytometry using αCD11c and FITC. The data showed migration of DCs from both syngeneic and rejecting grafts at a level of about 20-65,000/LN or 2-6%, which is significant and consistent with the literature (Kabashima, et al. (2007) *Am. J. Pathol.*

171:1249-57; Pham, et al. (2007) *Neoplasia* 9:1130-7; Suto, et al. (2006) *J. Immunol.* 176:4102-12). However, when the frequency of DCs was evaluated from the tolerant graft, it was in excess of 400,000/LN or 30%. Enhanced DC migration was observed in three separate experiments and in tolerant allografts on day 30 post-transplant. This data indicates that factors, like retinoic acid, produced within the tolerant allograft enhances DC migration to the regional LN, and as such, this high level of integration of the graft and the regional LN may be necessary to sustain active, dominant immune tolerance.

Graft tolerance and the role of $T^{reg}$ in wild-type B6 mice have been extensively studied and long-term graft survival in these mice has been tracked. Moreover, the cellular dynamics in the regional LN as well as the infiltration of $CD4^+Foxp3^+$ T cells into the tolerant allograft have been analyzed. In addition to the analysis of graft tolerance in wild-type B6 mice, a $T^{reg}$-dependent model of skin allograft tolerance is used to incisively track the behavior of alloreactive $T^{eff}$ and $T^{reg}$. This $T^{reg}$-dependent model of skin allograft tolerance relies on the development and infiltration of TCR Tg $T^{eff}$ and $T^{reg}$ into the graft and expansion in the regional LN. The use of both CD4 and CD8 TCR Tg T cells to follow the fate of the alloreactive T cell effectors and $T^{reg}$ have been analyzed in this system, thereby allowing the "visualization" of both graft rejection and tolerance (Quezada, et al. (2004) *Annu. Rev. Immunol.* 22:307-28; Quezada, et al. (2003) *Blood* 102:1920-6 (2003); Gonzalez, et al. (2002) *J. Immunol.* 169: 5581-9; Buhlmann, et al. (1999) *J. Immunol.* 162:4373-6). Overlaid into this system, strategies have been developed that allow for the control of retinoic acid signaling, and subsequent tracking of the cellular and functional consequences in allograft tolerance. Retinoic acid signaling is modulated by: depletion or supplementation in the diet for Vitamin A, the use of RAR/RXR-specific inhibitors, over-expression of the DN RARα in the CD4 lineage, and Cre-mediated deletion of the RXRα receptor in the CD4 lineage.

The data presented herein shows that DST/αCD154 tolerized mice on a short or long-term VitA$^{-/-}$ diet cannot retain allogeneic skin grafts and begin to develop histological features of graft rejection in the tolerized host. Based on these findings, it is determined whether the impact of Vitamin A deficiency is on the $T^{reg}$ compartment directly. This is carried out using an adoptive transfer model to evaluate allospecific $T^{reg}$ function (Jarvinen, et al. (2003) *Transplantation* 76:1375-9). Wild-type BE mice (on normal diet or Vitamin A$^{-/-}$ diet are tolerized with DST/αCD154 for 1 week. After one week, the LN are taken and adoptively transferred into RAG$^{-/-}$ mice grafted with an $F_1$ skin graft three weeks prior. If the source of LN cells are "tolerant," no rejection is seen in the grafted RAG$^{-/-}$ recipient, however, if $T^{reg}$ function is impaired, rejection is apparent. An example of this approach is presented, wherein αIL9 was used to block the development of $T^{reg}$ in the donor, and rejection was shown upon adoptive transfer. In addition, (using the B6 Foxp3-GFP as donor), $T^{reg}$ vs non-$T^{reg}$ can be electronically-cell sorted from the donor, specifically showing that Vitamin A$^{-/-}$ diet exerts its impact on impairing the development of alloreactive $T^{reg}$. Using the following transfer scheme depicted in Table 2, it can be shown that Foxp3$^+$ T cells from Vitamin A$^{-/-}$ mice which have been tolerized are defective in mediating tolerance in the grafted RAG$^{-/-}$ recipient. It is believed this is due to the inability of the alloreactive $T^{eff}$ to convert to a$T^{reg}$ in the absence of Vitamin A.

TABLE 2

| Donor Diet* | Treatment | Foxp3− | Fox3p+ | Rejection (R)/Tolerance (T) |
|---|---|---|---|---|
| Control or VitA$^{-/-}$ | None | + | − | R |
| | None | + | + | R |
| | None | − | + | T |
| | None | + | + | R |
| Control | Tolerized | + | − | R |
| | Tolerized | + | + | T |
| | Tolerized | − | + | T |
| VitA$^{-/-}$ | Tolerized | + | − | R |
| | Tolerized | + | + | R |
| | Tolerized | − | + | T |

*Diet refers to the source of Foxp3+ T cells. Foxp3 T cells are derived from wild-type control or tolerized mice.

To directly test for defectiveness in the $T^{reg}$ compartment, wild-type $T^{eff}$ are co-transferred with $T^{reg}$ from tolerized wild-type (thereby transferring tolerance) or transferred with $T^{reg}$ from mice on a Vitamin A$^{-/-}$ diet (it is expected that this will not transfer tolerance). This approach allows for the detection of defective tolerization in the $T^{reg}$ compartment following αCD154 and DST. This approach can be expanded to test sorted $T^{reg}$ (GFP$^+$) from the following sources: tolerized mice treated with pan-RAR antagonists LE540, and LGD-100815 (100 µg/mouse/every 3 days) prior to tolerance induction; tolerized DN-RARα mice; tolerized and CD4-cre-RXRα$^{FLOX}$ mice. Both the CD4-DN-RARα and the CD4-cre-Rα$^{FLOX}$ are intercrossed with the B6-Foxp3-GFP to allow indisputable sorting of $T^{reg}$.

It is expected that the selective impairment of retinoic acid signaling in the CD4 lineage will interfere with the induction of function $T^{reg}$ in this in vivo tolerance assay.

The aforementioned studies show a functional impairment of $T^{reg}$ development in mice in which retinoic acid signaling is impaired. To track the behavior and function of alloreactive CD4$^+$ and CD8$^+$ T cells in allogeneic skin rejection and tolerance, the co-adoptive transfer of two TCR Tg T cells are employed (Quezada, et al. (2004) supra; Quezada, et al. (2003) supra). Either individually, or together, these Tg T cells mediate the development and/or the rejection of allogeneic skin. 2C CD8$^+$ TCR Tg mice express a TCR which recognizes SIYRYYGL (SYG; SEQ ID NO:1) peptide in association with K$^b$ (syngeneic) and QLSPFPFDL (QL9; SEQ ID NO:2) associated to L$^d$ (allogeneic). QL9 forms part of the natural sequence of a Krebs enzyme cycle 2-oxoglutarate dehydrogenase and belongs to the endogenous peptide repertoire of H2$^d$ bearing APCs. TEa CD4$^+$ TCR Tg cells recognize the peptide ASFEAQGLANIAVDKA (SEQ ID NO:3) that correspond to the positions 52-68 from the alpha chain of Class II molecule I-E and is naturally expressed in all APCs from H2$^b$/I-E$^+$ strains (B6 mice are I-E$^-$ but their $F_1$ hybrids with BALb/c are I-E$^+$). These Tg T cells can be transferred alone and/or together, and their fate and function can be followed during tolerance induction or during GVHD or as a consequence of allogeneic skin rejection. To follow the development of a$T^{reg}$ in this system, TEa CD4$^+$ Foxp3-GFP TCR Tg have been used. Sort-purified TEa CD4$^+$ Foxp3-GFP$^{(-)neg}$ cells are transferred into tolerized mice and the transition of TEa CD4$^+$ Foxp3-GFP$^{(-)neg}$->TEa CD4$^+$ Foxp3-GFP$^{+(pos)}$ is tracked as a measure of a$T^{reg}$ differentiation in the tolerant allograft. The existing TEa-Foxp3-GFP can be intercrossed with the CD4-DN-RARα and the CD4-cre-RXRα$^{FLOX}$. This allows for the direct tracking of the expansion and differentiation of the TEa $T^{reg}$ when retinoic acid signaling is intrinsically impaired in these cells, and all of the functional manifestations of that effect.

Three systems have been employed for inducing the conversion of $T^{eff}$->$T^{reg}$; soluble antigen, tumor-derived antigen and alloantigen (see Table 3).

TABLE 3

| System | Admin. Antigen | $T^{eff}$ | Conversion | Agonist | Measure |
|---|---|---|---|---|---|
| Soluble Peptide | i.v. | OTII-GFP-Foxp3- | PLN | Vitamin A RA RARα, RARβ, RARγ RXR | $T^{eff}$-> $T^{reg}$ Expansion Function |
| Tumor | B16-OVA | OTII-GFP-Foxp3- | Tumor site and DLN | | |
| Alloantigen | DST/ Allograft | Tea-GFP-Foxp3- | Allograft and DLN | | |

RA, Retinoic Acid

These systems allow both functional assessment (graft tolerance, tumor immunity) and visual tracking of the fate of $T^{eff}$->$T^{reg}$ with regard to expansion and differentiation. Using these systems, the impact of retinoic acid agonists is evaluated. This includes a diet high (250-IU/g) in Vitamin A (Keyes, et al. (2007) *J. Nutr.* 137:1713-7; Kheirvari, et al. (2006) *J. Nutr. Sci. Vitaminol.* (*Tokyo*) 52:421-7; Ruhl, et al. (2007) *Mol. Nutr. Food Res.* 51:1173-81), direct administration of retinoic acid or the use of Tamibarotene, AM580 (RARα agonists), AC55649 (RARα agonist), CD437 (RARα agonist), a mixed RAR-RXR agonist (bexarotene with RXR>RAR activity), as well as pure RXR agonists (NRX4204 and LGD-100268). Dosing of these agonists range from 200-300 μg/mouse at least 3× week for multiple weeks. The extent of using the agonists in vivo largely depends on the initial in vitro studies that show efficacy of the agonists in $T^{eff}$->$T^{reg}$ conversion in vitro. It is expected that a high Vitamin A diet or the use of selective agonists will enhance $T^{eff}$->$T^{reg}$ conversion in vivo.

EXAMPLE 9

Vitamin A-Deficiency Interferes with the Development of Peripheral Tolerance

Figure 7A:
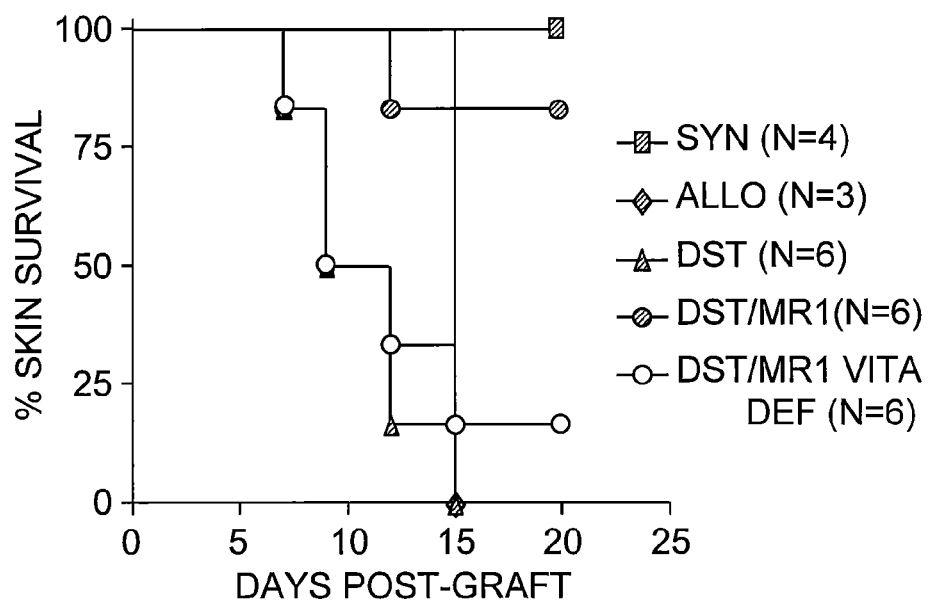
FIG. 7A depicts the effects of long-term VitA deficiency. C57BL/6 females were fed with VitA-deficient diet since day 7 of pregnancy. Offspring were weaned at 3 weeks of age, and fed with the same diet until use (6 weeks old). Seven days prior skin transplant, C57BL/6 mice (generated under regular (filled circle) and VitA-deficient diet (open circle)) were tolerized with DST from F1 mice plus αCD154. Mice were transplanted with C57BL/6 skin (Syngeneic, filled square) or F1 skin (Allogeneic, filled diamond, and DST alone treated recipients, filled triangle). Skin survival was monitored twice per week.

The analysis conducted herein shows that retinoic acid synergistically enhances the conversion of effector T cells ($T^{eff}$) to a$T^{reg}$ in vitro. Therefore, it was determined how to restrict the availability of retinoic acid in vivo by putting mice on Vitamin A-deficient (VitA) diets. Two alternatives are presented, both of which demonstrate an impact of VitA (and likely retinoic acid) on the survival of allografts in tolerized mice. First, pregnant moms were placed on a VitA-deficient diet, as were there offspring, resulting in long-term VitA-deprivation. The offspring were used at 6 weeks as hosts, at which time they are tolerized with DST and αCD154 and grafted. As can be seen in FIG. 7A, tolerized mice with DST and αCD154 (MR1) retained their grafts for over 20 days, and historically these grafts would survive for >80-100 days. Mice that were not tolerized (allo, DST alone) rejected their grafts by 15 days. Strikingly, 80% of the tolerized VitA-deficient mice lost their grafts by day 15. The impact of VitA was not a wound healing issue because syngeneic grafts onto VitA-def mice vascularized and healed normally.

Figure 7B:
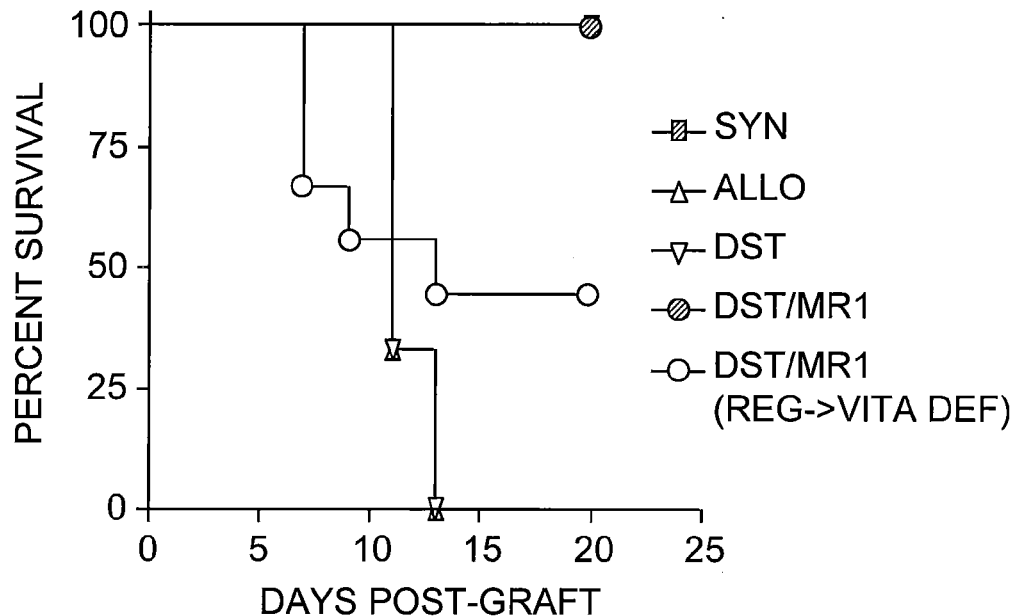
FIG. 7B depicts the effects of short-term VitA deficiency. Seven days prior tolerization regime (DST/MR1), adult C57BL/6 mice were switched from regular to Vitamin A-deficient diet with RAR inhibitors R041-5253 and LE540 administration three times per week (185 µg/mouse, i.p) and kept over the experiment (open circles).

In FIG. 7B, a short-term VitA-def approach was applied. Seven days prior tolerization regime (DST/MR1), adult C57BL/6 mice were switched from regular to VitA-deficient diets with RAR inhibitors R041-5253 and LE540 administration three times per week (185 μg/mouse i.p.) and kept over the experiment. This analysis indicates that 50% of adult mice that were tolerized and made VitA-deficient lost their grafts in 15 days. Taken together, the data indicates that retinoic acid regulates the generation of peripheral tolerance and the generation of $T^{reg}$.

To visualize the changes in cellular events of tolerance in VitA sufficient and VitA$^{-/-}$ recipients, immunofluorescence was employed. Rejecting skin was featured by the infiltration of CD8+ T cells and CD4+ T cells. In the tolerized graft (DST/MR1) there was an absence of CD8+ T cells, and some CD4+ T cells, but many expressed Foxp3. It was difficult to visualize Foxp3 this early during the tolerization process. In the tolerized, VitA−/− sections, there was clearly heightened infiltration of CD8+ T cells and CD4+ T cells and a near absence of Foxp3 staining. Thus, in the absence of Vitamin A, peripheral tolerance was either not induced and/or broke down. Retinoic acid synthesis by various organs was also ascertained using a retinoic acid reporter cell line (Wagner (1997) *Methods Enzymol.* 282:98-107), which is sensitive to sub-picomolar concentrations of retinoic acid. The data clearly showed that those mice that were on a Vitamin A-deficient diet were severely impaired in retinoic acid synthesis from liver and lymphoid organs.

Figure 8:
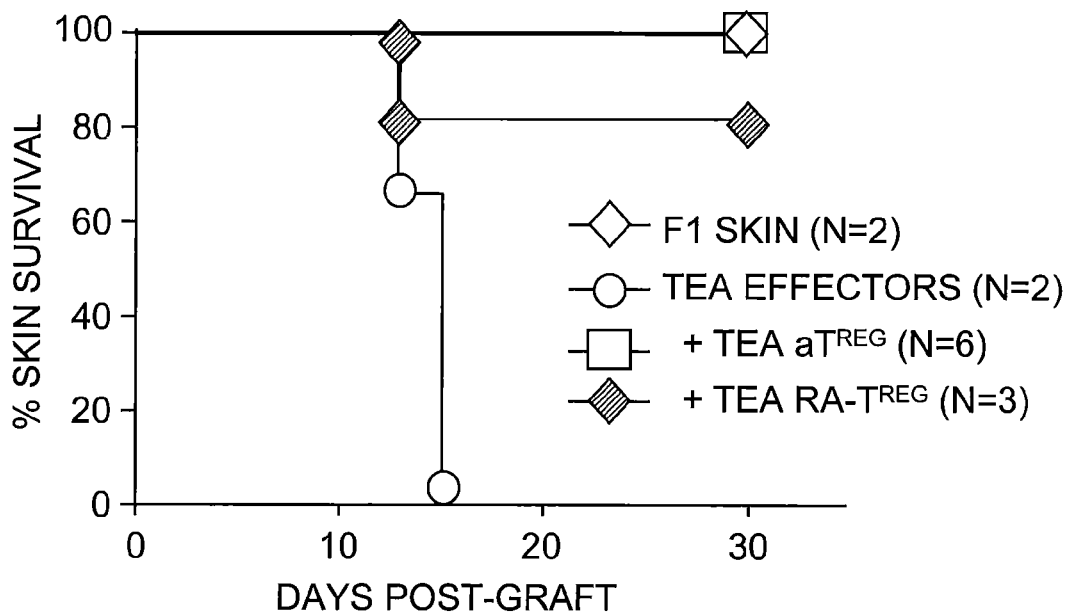
FIG. 8 shows that TEa aT$^{reg}$ and RA-T$^{reg}$ prevent graft rejection. Foxp3− TEa (100,000/mouse) were transferred alone, or with 100,000 Foxp3+ TEa aT$^{reg}$ or 100,000 Foxp3+ RA-T$^{reg}$ into RAGKO−/− mice. Survival was followed and data is representative of two such experiments.

Studies were also conducted to assess the functional activities of a$T^{reg}$ and RA-$T^{reg}$ in mediating graft tolerance in reconstituted RAG−/− mice. TEa Tg T Foxp3-GFP− cells were cultured with Ea peptide, irradiated APC, IL2, and TGFβ in the presence (RA-$T^{reg}$) or absence (a$T^{reg}$) of retinoic acid (1 nM). TEa effectors (Foxp3−) were transferred alone or together with sorted Foxp3+ TEa a$T^{reg}$ or Foxp3+ TEa RA-$T^{reg}$ and graft survival was monitored. As can be see in FIG. 8, the transfer of either TEa a$T^{reg}$ or TEa RA-$T^{reg}$ allowed for graft survival.

Figure 9:
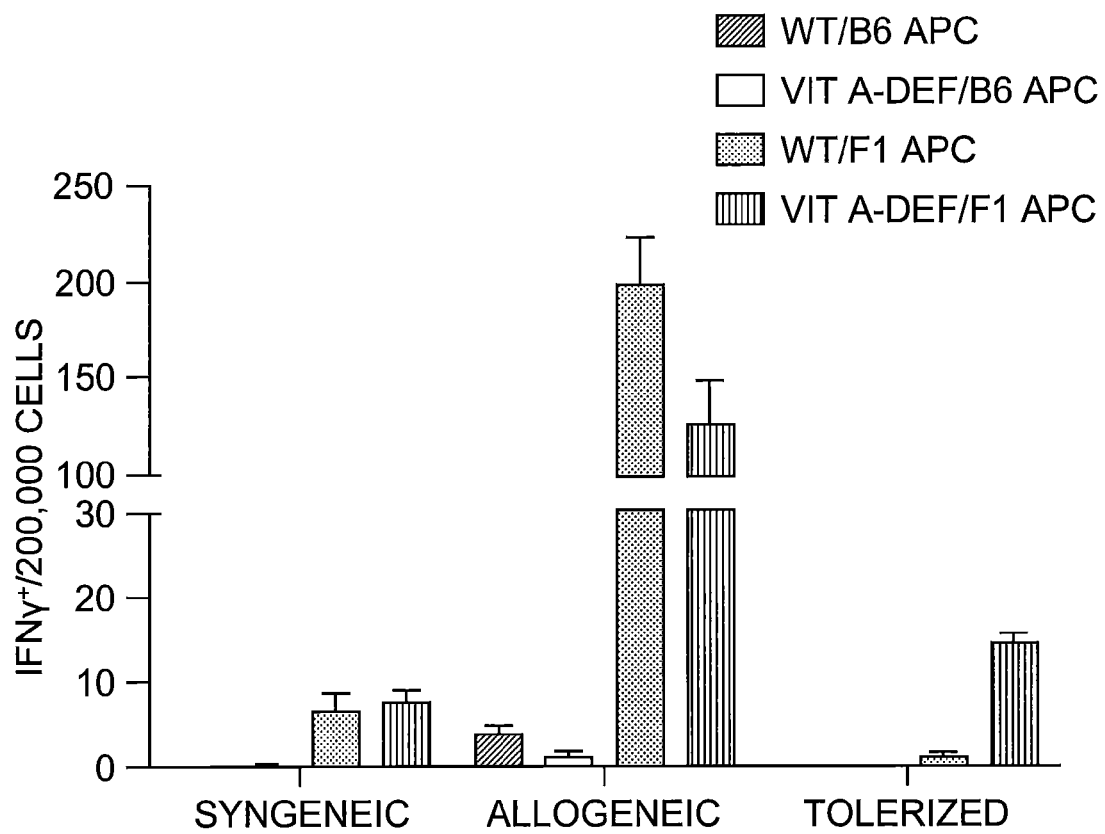
FIG. 9 shows the loss of tolerance due to Vitamin A deficiency. C57BL/6 females were fed a Vitamin A-deficient diet since day 7 of pregnancy. Offspring were weaned at 3 weeks of age, and fed with the same diet until use (6 weeks old). Seven days prior to skin transplant (with syngeneic or allogeneic skin), C57BL/6 mice (generated under regular and Vit A-deficient diet were tolerized with DST from F1 mice plus αCD154. Mice were transplanted with C57BL/6 skin (Syngeneic) or F1 skin (Allogeneic and DST alone treated recipients). On Day 7 after skin grafting, regional LN were recalled with alloantigen and the number of IFNγ-producing cells were enumerated.

In addition it was shown that tolerized mice on a VitA−/− diet begin to recover alloreactivity 7 days after tolerance is induced, whereas mice on a normal diet sustain their unresponsiveness to alloantigen (FIG. 9). It is contemplated that this is due to the inability to generate adaptive regulatory T cells.

EXAMPLE 10

In Vivo Models to Study $T^{eff}$->$T^{reg}$ Conversion

Intercrossing of the B6 Foxp3-GFP reporter mice with the TEa TCR Tg and the OTII TCR Tg (OVA) has afforded the opportunity to create systems to study the conversion of $T^{eff}$->a$T^{reg}$ in vivo in an antigen-specific manner. These models all use the transfer of sort-purified TCR Tg T Foxp3-GFP− into intact B6 mice and follow the conversion by congenic marking (Ly5.1 vs Ly5.2) or Vβ expression and GFP (for Foxp3). The analysis using these models was as follows.

$T^{eff}$->$T^{reg}$ in Graft Tolerance. B6 mice were either tolerized (DST/αCD154, day-7) or not, then grafted with syngeneic or allogeneic (F$_1$) skin. On day 0, TEa CD4+ T effector cells (CD4+CD25−Foxp3−GFP−) were sorted from pooled spleen and LN single cell suspensions, and injected i.v. at 1 million/ per B6 mouse. On day 14, grafts were isolated, single cell suspensions produced by enzymatic treatment and stained. Cells from the graft and draining LN were collected and analyzed by FACS for expression of Ly5.1, CD4 and GFP. Conversion was calculated as percentage of Foxp3-GFP+ cells among all transferred TEa CD4 T cells. Data presented in Table 4 is representative of at least three experiments.

$T^{eff}$->$T^{reg}$ with Soluble Antigen. OTII CD4+ T effector cells (CD4+CD25−Foxp3−GFP−) were sorted from pooled spleen and LN single cell suspensions, and injected i.v. at 1 million/per mouse on day 0. OVA peptide (ISQ; 25 µg)) was i.p. injected on the same day, as well as every three days for four additional times. Mice were sacrificed four days after the last injection, and cells from spleen and pooled LNs were collected and analyzed by FACS for expression of congenic marker Ly5.2, CD4 and GFP. Conversion was calculated as percentage of Foxp3-GF+ cells among all transferred OTII CD4 T cells Data presented in Table 4 is representative of at least two experiments.

$T^{eff}$->$T^{reg}$ with Tumor Antigen. OTII CD4+ T effector cells (CD4+CD25−Foxp3−GFP−) were sorted from pooled spleen and LN single cell suspensions, and injected i.v. at 1 million/per B6 mouse on day 0. Tumor cells (150,000 B16-OVA) were inoculated s.c. next day on the right flank. Mice were sacrificed when tumor size reached 0.8 cm×0.8 cm. Cells from tumor draining LN and tumor were collected and analyzed by FACS for expression of Ly5.1, CD4 and GFP. Conversion was calculated as percentage of Foxp3-GFP+ cells among all transferred OTII CD4 T cells. Data presented in Table 4 is representative of at least eight experiments.

TABLE 4

| Model | Input Cells | Output | Source | Range |
|---|---|---|---|---|
| Measure $T^{eff}$-> $T^{reg}$ in Anti-CD154/DST Model | B6 Foxp3− TEa Tg | B6 Foxp3+ TEa Tg | DLN Graft | 5-16% |
| Measure $T^{eff}$-> $T^{reg}$ in Model with Soluble OVA Immunization | B6 Foxp3− OTII TCR Tg | B6 Foxp3+ OTII TCR Tg | DLN Spleen | 5-15% |
| Measure $T^{eff}$-> $T^{reg}$ in Model with B16 Melanoma (Transduced with OVA) | B6 Foxp3− OTII TCR Tg | B6 Foxp3+ OTII TCR Tg | DLN Tumor | 5-70% |

In the first model, conversion was visualized within the tolerant allograft on day 14, but not in the DLN or in a syngeneic graft. In the soluble OVA system, conversion was readily observed with soluble OVA immunization in both the LN and the SPL as has been reported (Kretschmer, et al. (2006) *Nat. Protoc.* 1:653-61; Kretschmer, et al. (2005) *Nat. Immunol.* 6:1219-27). Finally, using OVA-transduced tumor, OTII conversion was observed in the DLN and at extremely high frequencies in the tumor mass. These models are also useful in hosts that are VitA$^{-/-}$ to evaluate whether retinoic acid is critical for conversion in each of these model systems.

EXAMPLE 11

Regulation of Retinoic Acid Synthesis within the Immune Privileged Microenvironment In chronic inflammatory disorders lymphoid neo-organogenesis is now recognized as an effort by the immune system to build a site with all of the anatomic hallmarks of an organized secondary lymphoid organ, to mediate inflammation. This was first appreciated in Rheumatoid Arthritis, and more recently in murine models of Multiple Sclerosis. The phrase "acquired immune privilege" has been used to designate sites which are destined to be protected, like a tolerant allograft or a tumor where the host builds an organized site to offset inflammation. It has been documented that there is a massive infiltration of cells into tumor sites and into tolerant allografts. In this regard, the accumulation of $T^{reg}$ and mast cells has been clearly shown and a role for tolerogenic DCs, myeloid suppressor cells, etc. has been documented. Within these sites, soluble mediators like TGFβ, IL10 and IL9 have been implicated in immune suppression. As presented herein, retinoic acid has been shown to play a pivotal role in the development of $T^{reg}$, in particular in mucosal immunity. Thus, this mediator plays a central role in "acquired immunologic privilege".

Studies suggest that the regulation of graft tolerance is regional or within the immune privileged microenvironment of the allograft. Substantive $T^{reg}$ accumulation within the immune privileged site has now been demonstrated, indicating that retinoic acid synthesis by hematopoietic cells controls the differentiation of $T^{reg}$ in the immune privileged microenvironment. However, stromal cells may also contribute to retinoic acid synthesis. It has now been shown that RALDH$^{+}$ cells can be found in the tolerant allograft. Thus, the factors that regulate the expression of RALDH and thereby control retinoic acid availability can be identified and it can be shown that retinoic acid synthesis by these cells is critical for the maintenance of immune tolerance.

It has been reported that RALDH expression can be identified in DCs from the MLN- and PP-DCs, but not PLN-DCs. Based upon the analysis disclosed herein, it is contemplated that LN DCs (and perhaps other hematopoietic and non-hematopoietic cells) do indeed make retinoic acid and that RALDH (terminal enzymes involved in retinoic acid synthesis and represent different isoforms) can be upregulated by signals within the immune privileged microenvironment. It has been shown that PPARγ agonists can induce DCs to synthesize retinoic acid (Szatmari, et al. (2006) *J. Exp. Med.* 203:2351-62). Immunofluorescent data, data with retinoic acid inhibitors, and RT-PCR data on tolerant allografts all indicate retinoic acid synthesis and RALDH expression in tolerant allografts.

RALDH immunofluorescence of allograft sections is also conducted. The advantage of RALDH immunofluorescence is that expression of a specific isoform (RALDH 1, 2, 3, 4, available commercially) can be correlated with lineage markers for specific leukocyte subsets. For example, cells can be co-stained with CD20 (B cells), CD11c (DCs), CD11c, CD8a$^{+}$ (lymphoid) or CD11c$^{+}$, CD8a-(myeloid), Mac 1 (macrophages) as well as T lineage markers (CD4, CD8), are expected to be negative. This immunofluorescence approach provides evidence as to the tissue distributed expression of RALDH.

Immunohistochemistry also provides insights into the cells likely to produce retinoic acid in the tolerant allograft. The RAR-reporter cell line (Wagner (1997) *Methods Enzymol.* 282:98-107) has been adapted for detection using the fluorescent substrate, fluorescein mono-β-D-galactopyranoside, such that retinoic acid reporting is sub-picomolar. Thus, cells can be sorted from syngeneic, rejecting and tolerant allografts and de novo retinoic acid synthesis can be immediately measured using this system to identify cells producing retinoic acid. It is anticipated that the cells detected as RALDH$^{+}$ will be concordant with those cells synthesizing retinoic acid.

What is claimed is:

1. A method for producing the isolated population of adaptive regulatory T cells comprising contacting an isolated effector T cell population with a retinoic acid in combination with transforming growth factor beta1 (TGFβ1) and interleukin-2 (IL-2) thereby producing a population of retinoic acid-induced adaptive regulatory T cells.

2. A method for treating an autoimmune response comprising administering to a subject exhibiting an autoimmune response an effective amount of the isolated population of retinoic acid-induced adaptive regulatory T cells produced by the method of claim 1, thereby treating an autoimmune response in the subject.

* * * * *

UNITED STATES PATENT AND TRADEMARK OFFICE
CERTIFICATE OF CORRECTION

| | | |
|---|---|---|
| PATENT NO. | : 8,415,154 B2 | Page 1 of 1 |
| APPLICATION NO. | : 12/601682 | |
| DATED | : April 9, 2013 | |
| INVENTOR(S) | : Randolph J. Noelle | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,154 B2
APPLICATION NO. : 12/601682
DATED : April 9, 2013
INVENTOR(S) : Randolph J. Noelle Page 1 of 1

It is certified that error appears in the above-identified patent and that said Letters Patent is hereby corrected as shown below:

In the Specification

Column 1, please delete Lines 11-14 and insert in its place the following:
--This invention was made with government support under grant number AI048667 awarded by the National Institutes of Health. The government has certain rights in the invention.--

Signed and Sealed this
Twenty-eighth Day of April, 2020

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Ser Ile Tyr Arg Tyr Tyr Gly Leu
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Gln Leu Ser Pro Phe Pro Phe Asp Leu
1               5

<210> SEQ ID NO 3
<211> LENGTH: 16
<212> TYPE: PRT
<213> ORGANISM: Artificial sequence
<220> FEATURE:
<223> OTHER INFORMATION: Synthetic peptide

<400> SEQUENCE: 3

Ala Ser Phe Glu Ala Gln Gly Leu Ala Asn Ile Ala Val Asp Lys Ala
1               5                   10                  15
```